(12) United States Patent
Velasco Valcke

(10) Patent No.: US 11,517,761 B2
(45) Date of Patent: Dec. 6, 2022

(54) TISSUE-STIMULATING METHOD USING SPATIAL SCANNING OF ELECTRIC AND MAGNETIC FIELDS

(71) Applicant: PANACEA QUANTUM LEAP TECHNOLOGY LLC, Dallas, TX (US)

(72) Inventor: Francisco Javier Velasco Valcke, Bogotá (CO)

(73) Assignee: PANACEA QUANTUM LEAP TECHNOLOGY LLC, Dallas, TX (US)

( * ) Notice: Subject to any disclaimer, the term of this patent is extended or adjusted under 35 U.S.C. 154(b) by 0 days.

(21) Appl. No.: 16/967,755

(22) PCT Filed: Feb. 7, 2019

(86) PCT No.: PCT/IB2019/051005
§ 371 (c)(1),
(2) Date: Aug. 6, 2020

(87) PCT Pub. No.: WO2019/155405
PCT Pub. Date: Aug. 15, 2019

(65) Prior Publication Data
US 2021/0038908 A1  Feb. 11, 2021

(30) Foreign Application Priority Data
Feb. 7, 2018  (CO) .......................... NC2018/0001282

(51) Int. Cl.
*A61N 2/02*  (2006.01)
(52) U.S. Cl.
CPC ..................................... *A61N 2/02* (2013.01)

(58) Field of Classification Search
CPC ...... A61N 2/00–12; A61N 1/04; A61N 1/323; A61N 1/36; A61N 1/36014; A61N 1/36034
See application file for complete search history.

(56) References Cited

U.S. PATENT DOCUMENTS 9,138,585 B2   9/2015  Saha et al.
9,278,231 B2   3/2016  Vasishta
(Continued)

OTHER PUBLICATIONS

International Search Report / Written Opinion dated Aug. 9, 2019 for PCT/IB2019/051005.
(Continued)

*Primary Examiner* — Thaddeus B Cox
(74) *Attorney, Agent, or Firm* — Fountainhead Law Group P.C.

(57) ABSTRACT

This disclosure refers to methods and devices for electromagnetic stimulation of tissues. Some methods comprising the steps: a) disposing an arrangement of electromagnetic transducers encompassing a volume containing a tissue; b) applying an electromagnetic field stimulus to a tissue through the arrangement of electromagnetic transducers according to an activation pattern for a period of time; wherein the activation pattern allows to vary the intensity and direction of the electromagnetic field vector. Some devices comprising: a computing unit, an external power source connected to the computing unit; a decoupling circuit connected to the external power source and to the computing unit; a switching circuit connected to the external power source, to the decoupling circuit and to the computing unit; an arrangement of electromagnetic transducers connected to the computing unit and to the de switching circuit; wherein the computing unit implements the methods of the disclosure for electromagnetic stimulation of tissues.

18 Claims, 11 Drawing Sheets

(56) References Cited

U.S. PATENT DOCUMENTS

| | | |
|---|---|---|
| 2010/0152817 A1 | 6/2010 | Gillbe |
| 2011/0307029 A1* | 12/2011 | Hargrove ............. A61B 5/4058 607/45 |
| 2012/0226200 A1 | 9/2012 | Wagner et al. |
| 2013/0090712 A1 | 4/2013 | Popovic et al. |
| 2017/0209708 A1 | 7/2017 | Schwarz |
| 2018/0078269 A1* | 3/2018 | Meinke .................. A61B 17/22 |
| 2018/0193658 A1* | 7/2018 | Hong ..................... A61N 2/006 |

OTHER PUBLICATIONS

International Preliminary Report on Patentability comleted Jun. 24, 2020 (dated Jul. 1, 2020) for PCT/IB2019/051005.

* cited by examiner

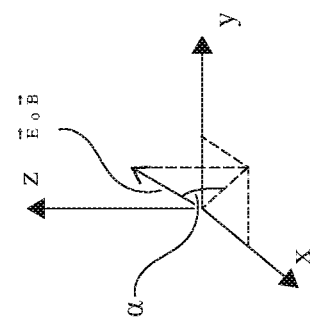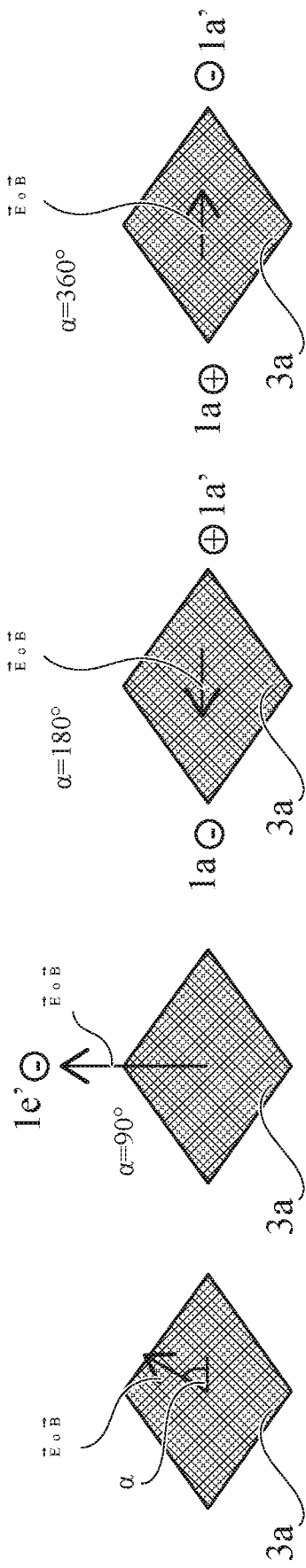

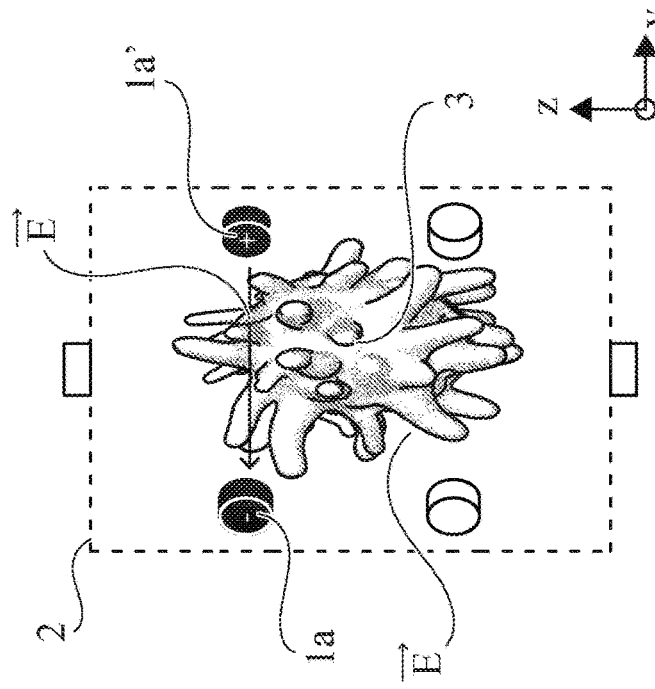
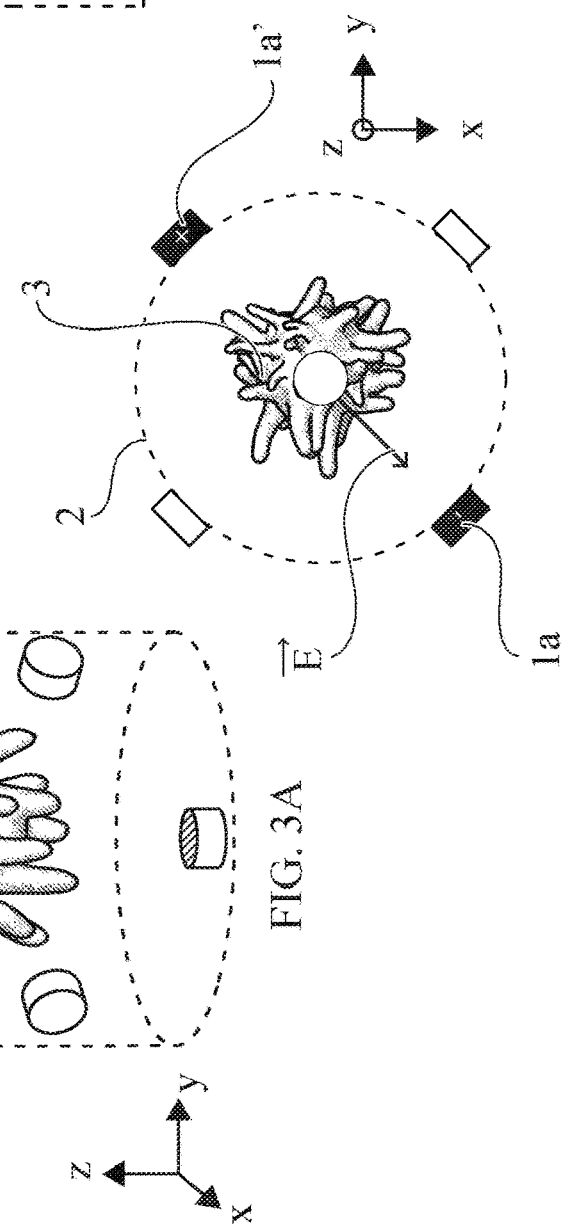
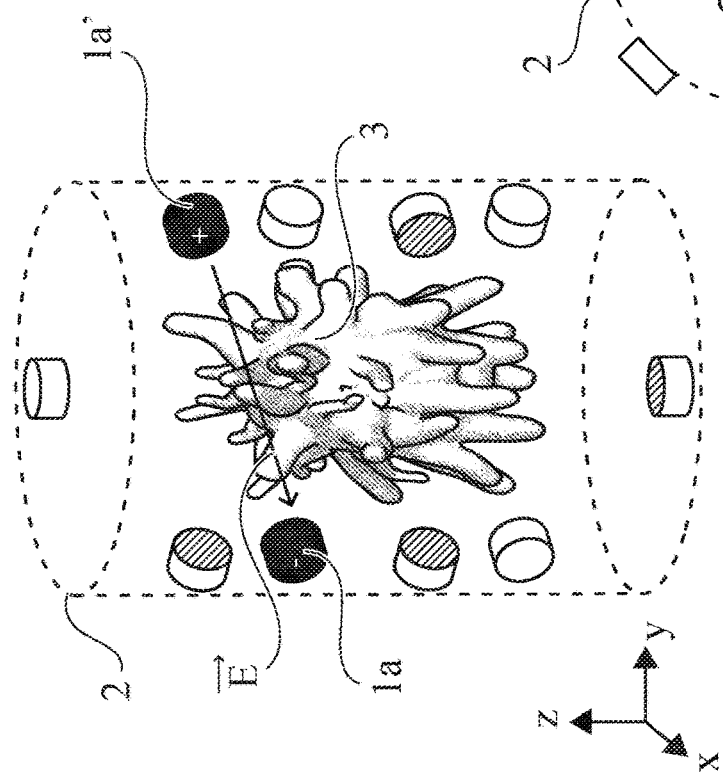
FIG. 3A
FIG. 3B
FIG. 3C

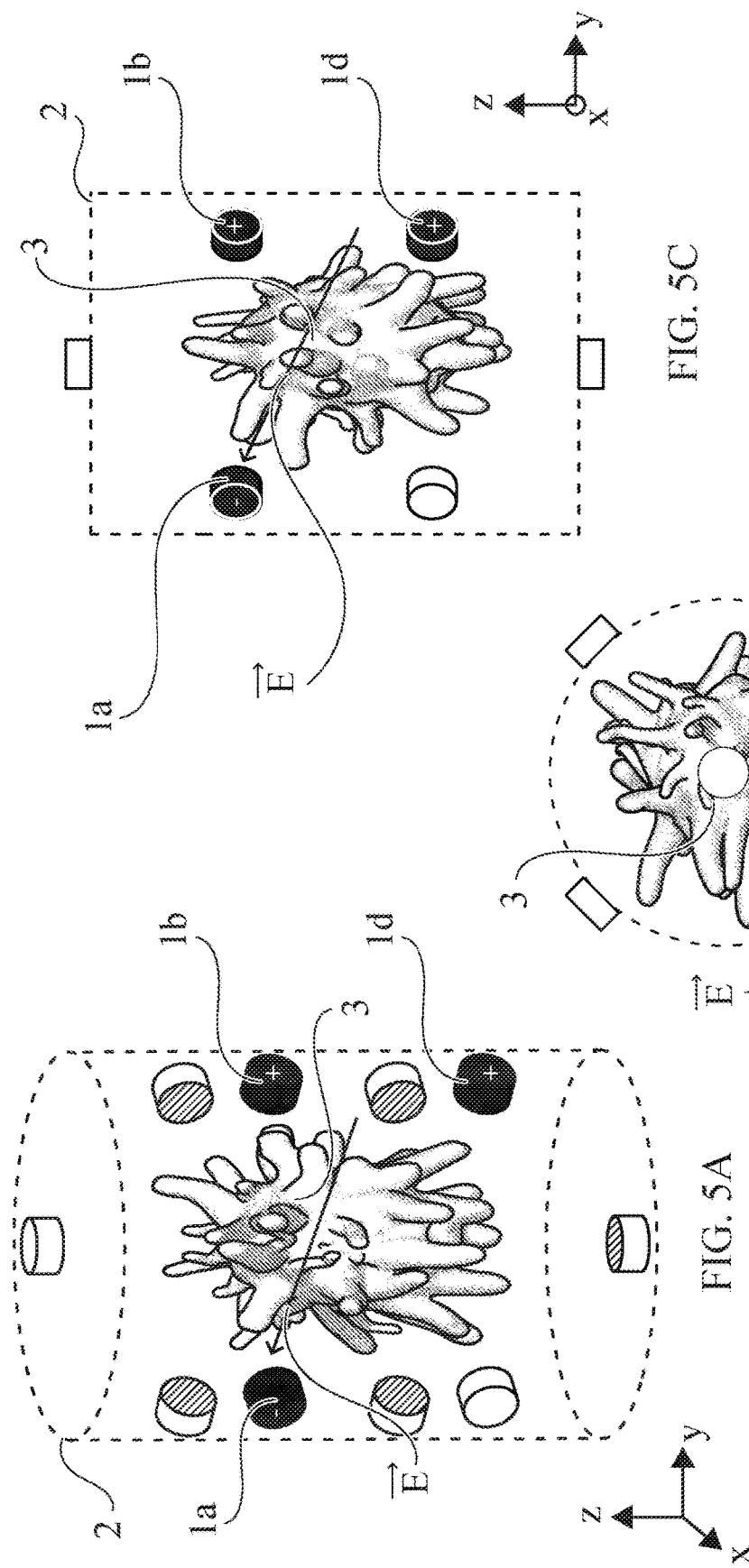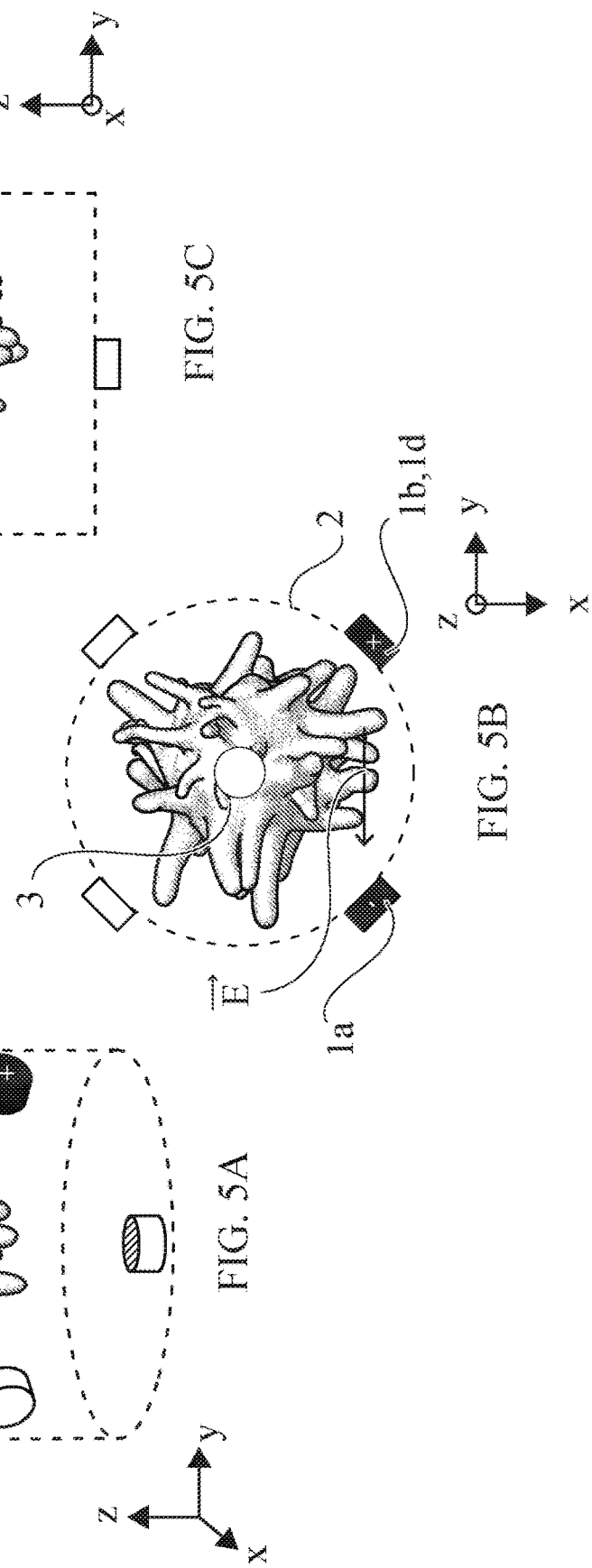

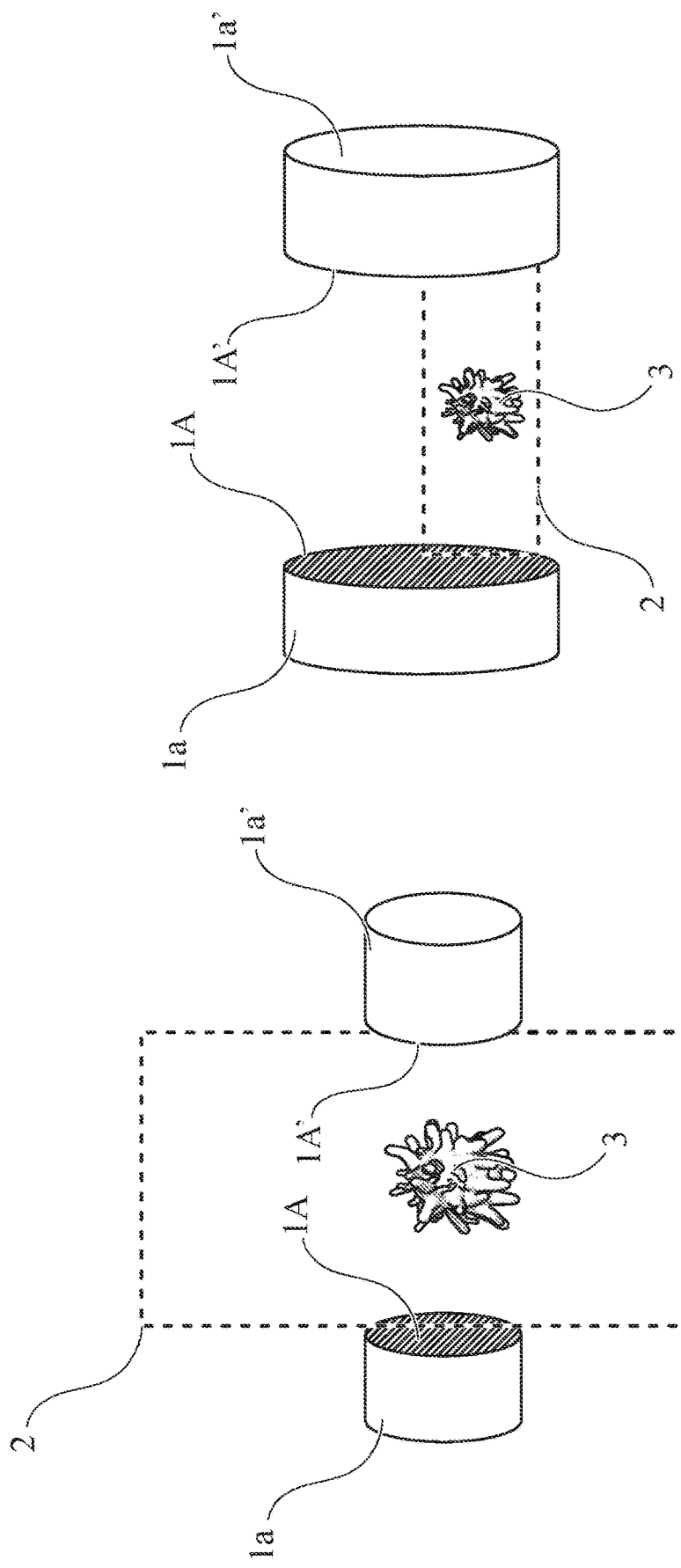

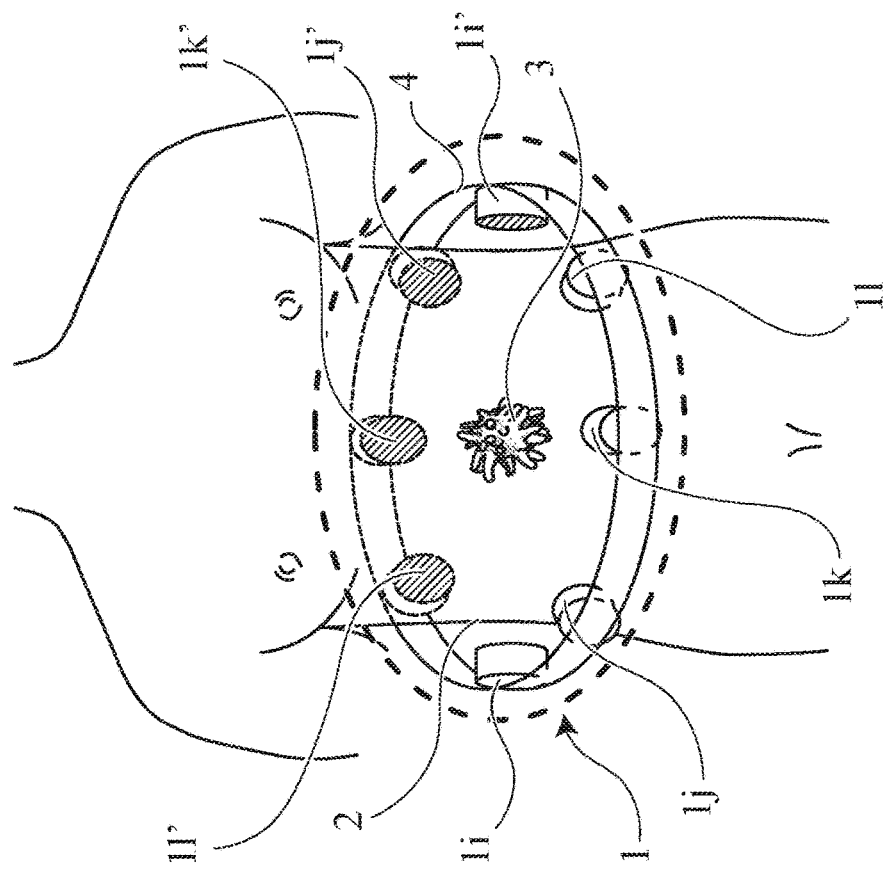
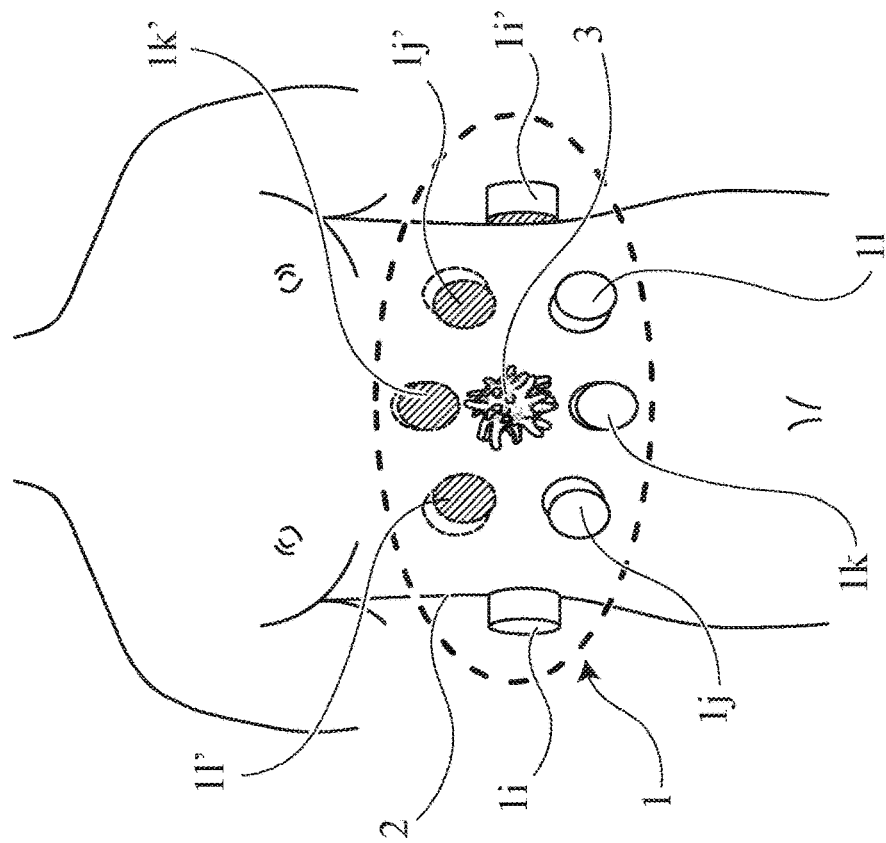
FIG. 8A
FIG. 8B

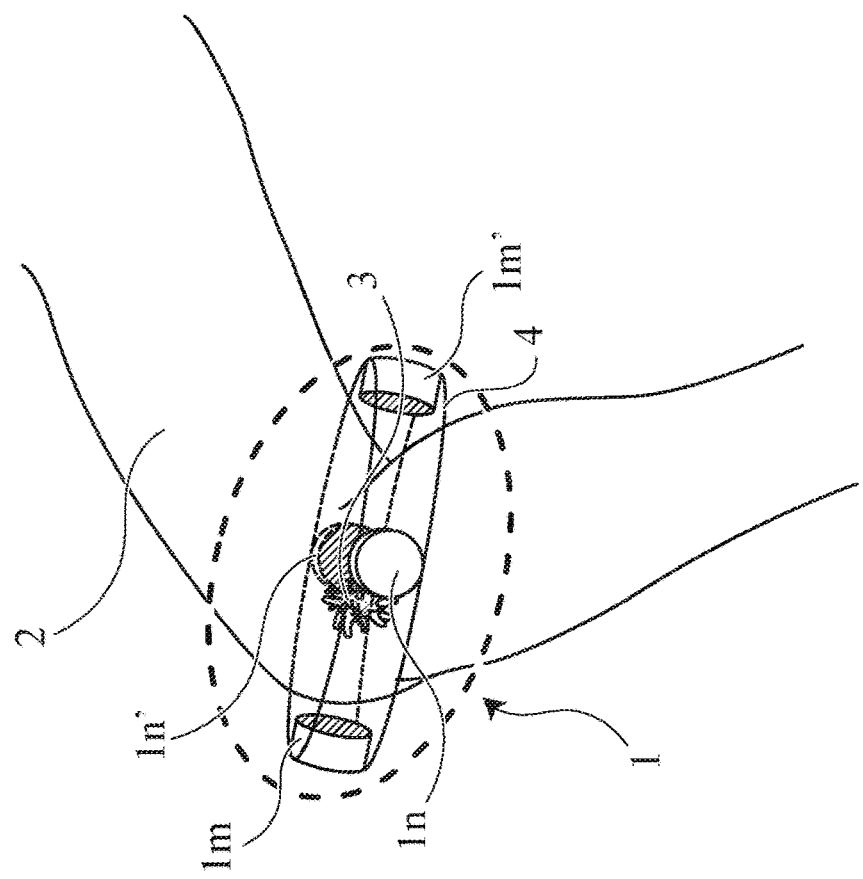
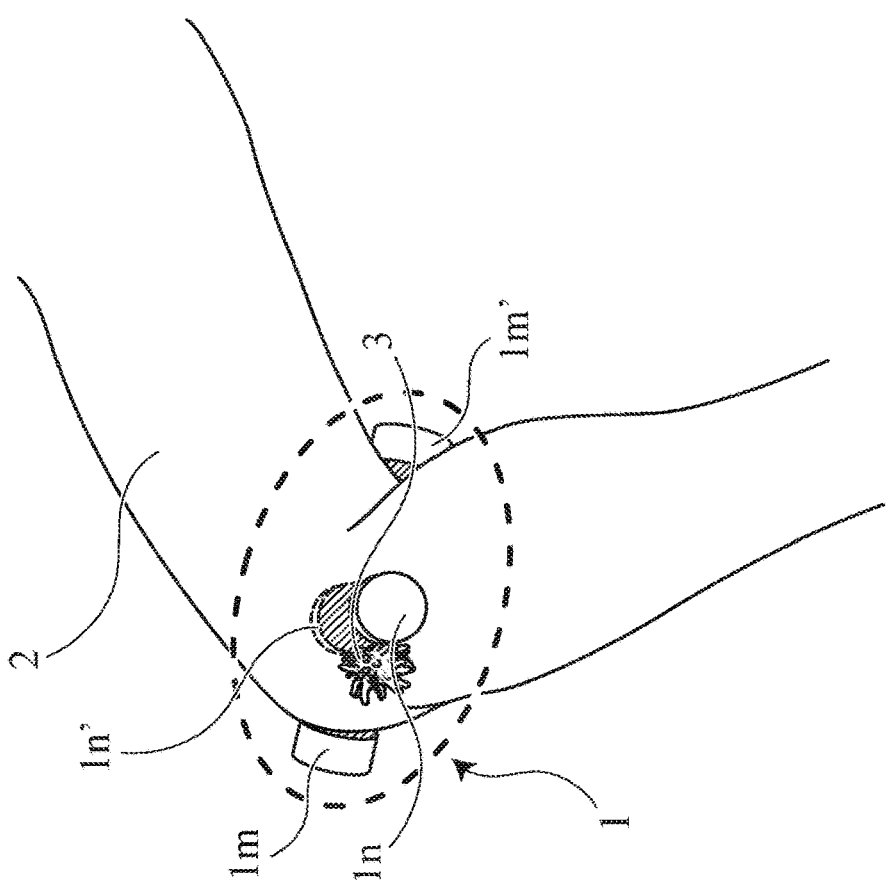
FIG. 9A
FIG. 9B

TISSUE-STIMULATING METHOD USING SPATIAL SCANNING OF ELECTRIC AND MAGNETIC FIELDS

CROSS-REFERENCE TO RELATED APPLICATION

This application is the National Stage of International Application No. PCT/IB2019/051005, filed Feb. 7, 2019, and claims the priority benefit of Colombia application serial no. NC2018/0001282, filed on 7 Feb. 2018. The entirety of each of the above-mentioned patent applications is hereby incorporated by reference herein and made a part of this application. The tissue stimulation disclosed in the present document is related to Colombian application serial no. NC2018/0001283, filed on 7 Feb. 2018.

The tissue stimulation disclosed in the present document is related to Colombian application serial no. NC2018/0001283, filed on 7 Feb. 2018.

BACKGROUND

Technical Field

This disclosure is related to methods for tissue stimulation with electromagnetic, electrical and magnetic fields. More specifically, the disclosure is related to tissue stimulation with electromagnetic, electrical and magnetic fields by spatial scanning, said spatial scanning referring to the variation of the electromagnetic, electrical or magnetic field vector in a three-dimensional space over its three axes.

Description of Related Art

A living organism moves, feeds off and interacts with its environment, through biochemical interactions, which, in addition, comprise the electrical activity of the organism.

This electrical activity can be measured in the form of currents and electrical fields and magnetic fields, which are recorded, for example, by electromyographs (EMG) which, in the case of electrical activity of the heart, are called electrocardiographs (ECG), and in the case of measuring the electrical activity of the brain, electroencephalographs (EEG).

Likewise, it is possible to influence the organism with electromagnetic fields, similar to how any material that is, or can be, electrically charged, is influenced. Studies have demonstrated that these fields, when applied to living organisms, can produce cellular regeneration and/or deterioration. In studies of the application of magnetic fields, areas of interest such as the rehabilitation of damaged or paralyzed muscle groups are included, such as, for example, magnetic stimulation of the heart and regeneration of bone tissue, among others.

On the other hand, there are studies of the application of electrical fields that include areas of interest such as the treatment of central nervous system disorders that deal with specific dysfunctional conditions such as, for example, fibromyalgia, chronic pain, attention deficit, bipolar disorder, chronic fatigue, sleep disorders, depression and anxiety, among others.

Methods have been disclosed for the electro-magnetic stimulation of tissues, such as, for example, those disclosed by U.S. Pat. No. 9,278,231 B2 and U.S. Pat. No. 9,138,585 B2.

U.S. Pat. No. 9,278,231 B2 discloses a device and methods for generating magnetic fields (MFG, Magnetic Field Generator); the device comprises an electrical coil rolled circumferentially in the magnetic field generating device, and also discloses an apparatus called SPMF (Sequentially Programmed Magnetic Field), which comprises an arrangement of MFGs to produce pulsed magnetic fields in a focused area, with the pulses being controlled by a switch operated system connected to a computer that generates a protocol based on an embedded logic that depends on the type of disease and the treatment to be administered.

U.S. Pat. No. 9,278,231 B2 describes a method applying a pulsed magnetic field to a target tissue, following an ordered sequential pattern with determined frequency ranges; in other modalities, the magnetic field is generated by a plurality of opposed pairs of MFGs that are activated simultaneously and out of phase, each pair of MFGs is activated in a pattern that follows a rotating arrangement.

However. U.S. Pat. No. 9,278,231 B2 does not disclose adjusting the position of the MFGs according to the shape of the tissue, which makes application of the magnetic field on the tissue inefficient.

U.S. Pat. No. 92,788,231 B2 also only describes the use of magnetic fields, and not electrical fields in combination. Since the technical effect of applying an electrical field to a tissue prevails over the effect of the magnetic field, the stimulation described is deficient compared to a stimulation combining magnetic and electric fields U.S. Pat. No. 9,278,231 B2 does not disclose any feedback for adjusting the activation pattern as a function of the progress of tissue stimulation, due to which it cannot be adapted to tissue variations during stimulation.

U.S. Pat. No. 9,278,231 B2 discloses that the variation of the magnetic field vector is achieved in a circular plane and not over other axes and therefore does not make it possible for the tissue to be stimulated where the field vector is slanted in relation to the circular plane, resulting in deficient tissue stimulation.

U.S. Pat. No. 9,138,585 B2 discloses a method for configuring a medical device to be used with a multipolar system of electrodes that comprises providing a user with an interactive graphic representation of electro stimulation vectors, receiving a selection of said vectors, providing a visual indication of said selection, interactively using said selection of vectors to execute an electro stimulation test on the tissue to be treated.

U.S. Pat. No. 9,138,585 B2 discloses that measurements of the impedance level can be taken for deciding to execute more tests, or to stop.

U.S. Pat. No. 9,138,585 B2 does not disclose that the application of the electrical field is adapted to tissue variations during treatment despite having measured tissue impedance, with the parameters of the application of the field having to be adjusted by a user via interaction with the interactive graphic representation of the electrical stimulation vectors.

U.S. Pat. No. 9,138,585 B2 is only applied invasively since an incision must be made through a tissue group in order to reach the target tissue, which may cause damage to healthy tissue in a risky and complex procedure, in order to implant the transducers.

U.S. Pat. No. 9,138,585 B2, even though it can be used for different types of tissues, is used primarily for the heart.

If indeed the state of the art includes documents that use methods with electrical fields and fields for the treatment of tissues, these are not adapted to tissue variations during treatment, nor are they applied so as to generate a variation in three-dimensional space of the electromagnetic field vectors, since they are limited to varying the electromagnetic field vectors in a plane, restricting the beneficial effects to the tissue.

SUMMARY

This disclosure refers to methods and devices for the electromagnetic stimulation of a tissue by spatial scanning, a method comprising the steps: a) disposing an arrangement of electromagnetic transducers encompassing a volume containing a tissue; b) applying an electromagnetic field stimulus to a tissue through the arrangement of electromagnetic transducers according to an activation pattern for a determined period of time; wherein the activation pattern makes it possible to vary the intensity and direction of an electromagnetic field vector produced by the arrangement of electromagnetic transducers. Said spatial scanning refers to the variation of the electromagnetic, electrical or magnetic field vector, in a three-dimensional space.

Optionally, after step (b), there is a step involving a change in the activation pattern and returning to step (b), where said change in the activation pattern can be executed by a user, can be programmed in a computing unit, or can be manually or automatically adjusted through a feedback. Said feedback may be an electromagnetic field intensity, tissue impedance response, temperature, tissue surface images, tissue impedance response, or combinations of these.

A device for stimulating a tissue with electromagnetic fields, the device comprising a computing unit, an external power source connected to the computing unit, a decoupling circuit connected to the external power source and to the computing unit, a switching circuit connected to the external power source, to the decoupling circuit and to the computing unit, and an arrangement of electromagnetic transducers connected to the computing unit and to the switching circuit; wherein the computing unit implements a method for electromagnetic stimulation of a tissue, the method comprising the steps of: a) disposing an arrangement of electromagnetic transducers encompassing a volume containing a tissue; and b) applying an electromagnetic field stimulus to a tissue through the arrangement of electromagnetic transducers according to an activation pattern for a determined period of time; wherein the activation pattern makes it possible to vary the intensity and direction of an electromagnetic field vector produced by the arrangement of electromagnetic transducers.

BRIEF DESCRIPTION OF THE DRAWINGS

FIG. 2A shows a coordinated, three-dimensional system in which an electrical or magnetic field vector is represented.

FIG. 2B shows an example of a tissue slice with a representation of an electrical or magnetic field vector with an angle in relation to plane xy.

FIG. 2C shows an example of a tissue slice with a representation of an electrical or magnetic field vector at an angle of 90 degrees in relation to plane xy.

FIG. 2D shows an example of a tissue slice with a representation of an electrical or magnetic field vector at an angle of 180 degrees in relation to plane xy.

FIG. 2E shows an example of a tissue slice with a representation of an electrical or magnetic field vector at an angle of 360 degrees in relation to plane xy.

FIG. 3A shows a diagram of an arrangement of transducers in which the activation pattern of an initial time 1 activates a pair of electromagnetic transducers, in top view.

FIG. 3B shows a diagram of an arrangement of transducers in which the activation pattern of an initial time 1 activates a pair of electromagnetic transducers, in top view.

FIG. 3C shows a diagram of an arrangement of transducers in which the activation pattern of an initial time 1 activates a pair of electromagnetic transducers, in frontal view.

FIG. 5A shows a diagram of an arrangement of transducers in which the activation pattern of an initial time 3 activates a pair of electromagnetic transducers, in isometric view.

FIG. 5B shows a diagram of an arrangement of transducers in which the activation pattern of an initial time 3 activates a pair of electromagnetic transducers, in top view.

FIG. 5C shows a diagram of an arrangement of transducers in which the activation pattern of an initial time 3 activates a pair of electromagnetic transducers, in frontal view.

FIG. 6A shows a diagram in which two electromagnetic transducers have their active faces facing each other in co-linear form.

FIG. 6B shows a diagram in which two electromagnetic transducers with their active faces facing each other in co-linear form and a portion of the area of their active faces is in contact with the tissue and another portion of their active faces are spaced apart from the tissue.

FIG. 8A shows an example of the placement of an arrangement of electromagnetic transducers in contact and targeting a tissue in the abdominal area of an individual.

FIG. 8B shows an example of the placement of an arrangement of electromagnetic transducers without contact and targeting a tissue in the abdominal area of an individual.

FIG. 9A shows an example of the placement of an arrangement of electromagnetic transducers in contact and targeting a tissue in the knee area of an individual.

FIG. 9B shows an example of the placement of an arrangement of electromagnetic transducers without contact and targeting a tissue in the knee area of an individual.

DETAILED DESCRIPTION

This disclosure discloses methods and devices for the electromagnetic stimulation of tissues by spatial scanning of an electromagnetic field, said spatial scanning referring to the variation of the electromagnetic, electrical or magnetic field vectors in a three-dimensional space via the activation of an arrangement of electromagnetic transducers and the field vector is the vector resulting from various transducers of the arrangement of electromagnetic transducers simultaneously acting on the tissue.

One of the effects of electromagnetic stimulation of tissues by spatial scanning is to achieve a better distribution of an electromagnetic energy associated with said stimuli, in other words a better dosage of electromagnetic stimulation to the tissues being stimulated.

Another effect of electromagnetic stimulation of tissues by spatial scanning is the superior performance of the device for the electromagnetic stimulation of tissues by spatial scanning since the power supplied by an external power source is dosed according to a feedback, for example, according to tissue impedance response.

The methods for the electromagnetic stimulation of tissues by spatial scanning of an electromagnetic field permits to avoid overheating of the array of electromagnetic transducers by using a specific activation pattern to vary the intensity and direction of an electromagnetic field vector produced by the arrangement of electromagnetic transducers of the device.

Figure 1:
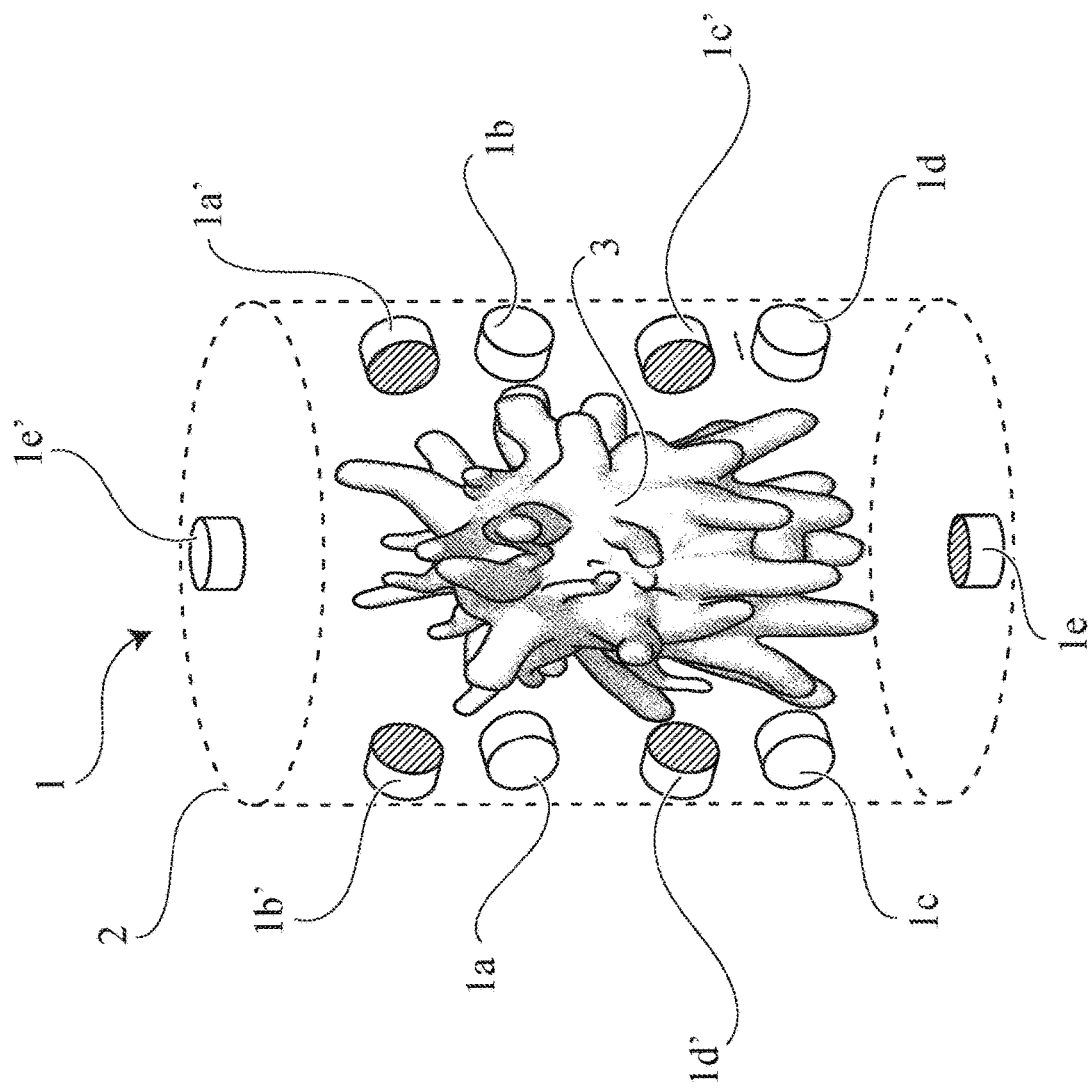
FIG. 1 shows an example of an arrangement of transducers over a volume containing a tissue.

In reference to FIG. 1, a flow diagram of an example of a method of the present disclosure, the method of electromagnetic stimulation of a tissue comprising the following steps: step a) disposing an arrangement of electromagnetic transducers (1) encompassing a volume (2) containing a tissue (3); step b) applying an electromagnetic field stimulus to a tissue through the arrangement of electromagnetic transducers (1) according to an activation pattern for a determined period of time, wherein the activation pattern makes it possible to vary the intensity and direction of an electromagnetic field vector produced by the arrangement of electromagnetic transducers (1) in a three-dimensional space in an xyz axe coordinate system. "x". "y" and "z".

Tissue refers to the biological tissues of living beings comprised of one or more cells, may be constituted by cells of only one class, all the same, or by various types of cells arranged in an orderly fashion to form an organ or an organism. The cited tissue may be healthy tissue, such as epithelial tissue, connective tissue, muscle tissue, nerve tissue or combinations of these. The tissue may also be a tissue with a total or partial bio-chemical imbalance in healthy tissue, said bio-chemical imbalance in turn may correspond to benign, neoplastic tissue, malignant neoplastic tissue or any cell out of homeostasis or in homeostasis. Also, tissue may refer to cells in vivo or prior to implantation said cells into an in vivo environment.

The tissue may come or be from animals including, without limitation: mammals, avian species, including chickens, turkeys, geese and ducks; fish, crustacean species (shrimp, lobsters, crayfish); and reptiles such as crocodiles and alligators. The term "mammal" as used herein refers to any mammal classified as a mammal, including humans, non-human primates, such as cynomolgus monkey, chimpanzees, baboon and gorilla; domestic and farm animals including equine species, bovine species, swine species, caprine species, canine species, feline species, ovine species, rabbits, llamas; ungulates, such as bovine, ovine, porcine, equine, caprine, canine, feline, murine, rabbit; and rodents such as guinea pigs, hamsters and rats.

The electromagnetic stimulation of a biological tissue or stimulation of a tissue refers to administering energy to said biological tissue in order to induce certain changes the characteristics of said biological tissue such as tissue impedance response, tissue vascularization, tissue temperature, tissue health, tissue growth rate, among others.

Figure 10:
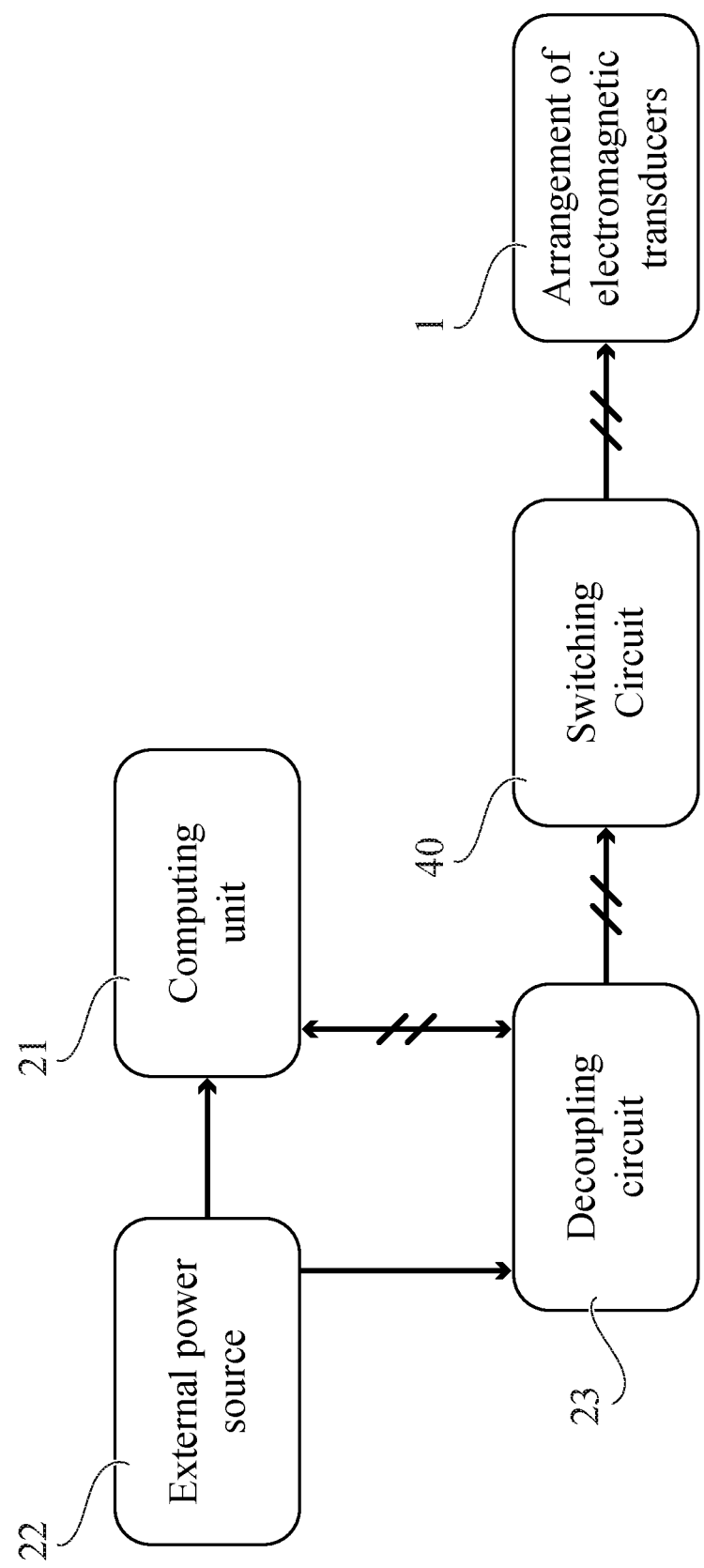
FIG. 10 shows a block diagram of an example of a tissue stimulating device of this disclosure.

In reference to FIG. 10, an example of a tissue stimulating device of the present disclosure is shown, the tissue stimulating device comprises a computing unit (21), an external power source (22) connected to the computing unit (21), a decoupling circuit (23) connected to the external power source (22) and to the computing unit (21), a switching circuit (40) connected to the decoupling circuit (23), an arrangement of electromagnetic transducers (1) connected to the switching circuit (40), wherein the computing unit (21) implements the method for tissue stimulation with a spatial scanning of electric fields, the method for tissue stimulation with a spatial scanning of magnetic fields, and methods that combine spatial scanning having electrical fields and magnetic fields, and may be configured with the tissue stimulating device in order to generate an activation pattern that activate the electromagnetic transducers of the arrangement of electromagnetic transducers, electric field or magnetic field through the switching circuit (40).

Optionally, the computing unit (21) implements a method for electromagnetic stimulation of a tissue, the method comprising the steps of: a) disposing an arrangement of electromagnetic transducers encompassing a volume containing a tissue; and b) applying an electromagnetic field stimulus to a tissue through the arrangement of electromagnetic transducers according to an activation pattern for a determined period of time; wherein the activation pattern makes it possible to vary the intensity and direction of an electromagnetic field vector produced by the arrangement of electromagnetic transducers, electric field or magnetic field through the switching circuit (40).

Optionally, the connection made between, the switching circuit (40), the arrangement of electromagnetic transducers (1) and the decoupling circuit (23) is made using a data bus.

As used herein, a bus refers to a plurality of connectors or set of wires that provides transportation for data, said data may be, for example, the activation signal or related to the activation pattern.

Said tissue stimulating device may also be understood as a device for stimulating a tissue with electromagnetic fields or, a device for stimulating a tissue with electrical fields and magnetic fields or simply a device for stimulating a tissue.

Figure 11:
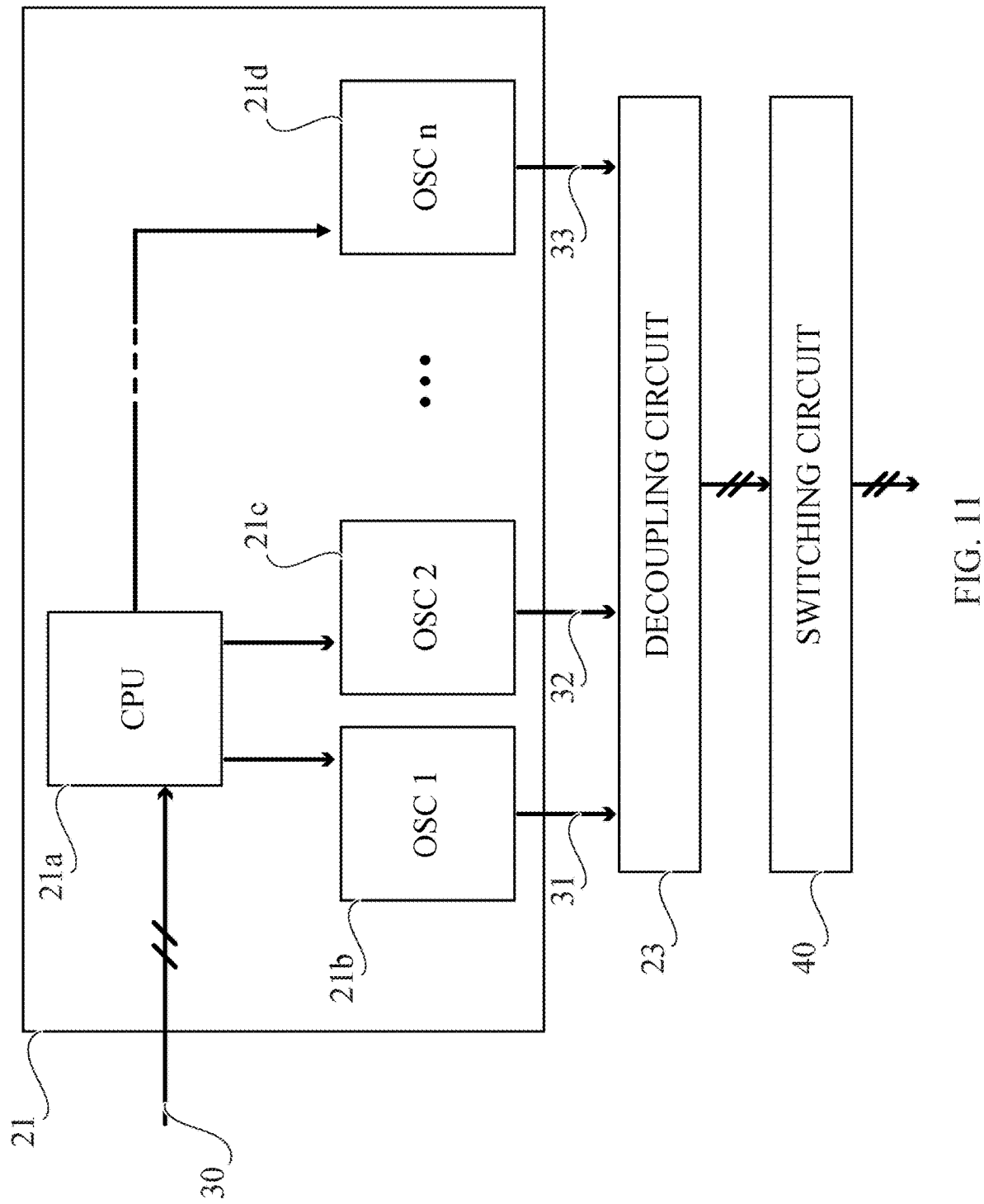
FIG. 11 shows a block diagram of an example of a special purpose computing unit of a tissue stimulating device of this disclosure.

In reference to FIG. 11, an example in which the computing unit (21) is a special purpose computing unit comprising a central processor unit (CPU) (21a) connected to oscillators from a first OSC 1, a second oscillator OSC 2 to an oscillator OSC n, each oscillator having an activation signal output (31-33); wherein "n" is a natural number equal or greater than zero. According to this, the computing unit (21) may have a maximum of "n" outputs. Optionally "n" is a value of between about 1 and about 1000, alternatively "n" is 1 and optionally 200, without being bounded to this values. Activation signal outputs may also be named as channels.

As used herein "about" refers to +20% to −20% variation.

Optionally, the activation signal outputs (31, 32 and 33) of each oscillator is connected to the arrangement of electromagnetic transducers (1) directly or through a decoupling circuit (23).

Alternatively, the activation signal outputs (31, 32 and 33) of each oscillator is connected to the arrangement of electromagnetic transducers (1) directly or through a switching circuit (40) which is connected to the CPU (21a).

Alternatively, the CPU (21a) is also connected to a peripheral device selected among others, from storage devices such as a memory unit, a database and a hard drive, input devices such as a keyboard, a camera, a touchscreen display, and a scanner, output devices such as a display, a printer and a printer.

In another example of the tissue stimulating device, the oscillators are replaced by signals generators.

Optionally, the parameters of each activation signal such as frequency, phase, amplitude, duty cycle, can be modified by instructions of a remote computing unit, by a user through an HID connected to the tissue stimulating device.

The computing unit (21) of the tissue stimulating device may use feedback (30), for example, a tissue impedance response feedback in order to dynamically adjust the activation signal outputs (31-33) which are received by the transducers and applied to the tissue to stimulate it.

Feedback (30) is a mechanism by which a certain portion of the output of a tissue stimulation device is redirected to the input, for the purpose of controlling its behavior. For example, when stimulating the tissue with electrical fields, magnetic fields or both, there may be a variation in tissue impedance response. Tissue impedance response feedback can be achieved by employing electric field transducers, said feedback making it possible to perceive variations in the tissue impedance response and to dynamically adjust the activation signal.

Alternatively, feedback (30) is not limited to obtaining the tissue impedance response to the tissue stimulus, said feedback may be a bus carrying measuring data pertaining to the tissue. For example, feedback (30) may incorporate, measuring the temperature in order to determine tissue fatigue, images of the tissue surface in order to determine tissue vascularization, tissue impedance response measurements, or combinations of these.

When stimulating the tissue with electrical fields, or magnetic fields, or both fields, there may be increments of temperature on the surface of the tissue. A temperature sensor or temperature measuring device may be used to perceive temperature variations and to dynamically adjust the activation pattern of electrical fields, magnetic fields, or both fields, in order to avoid lesions on the tissue due to overheating.

In order to understand this disclosure, a computing unit is a device that processes data, for example, microcontrollers, microprocessors, DSCs (Digital Signal Controllers), FPGAs (Field Programmable Gate Arrays). CPLDs (Complex Programmable Logic Devices), ASICs (Application specific Integrated Circuits), SoCs (Systems on Chip), PSoCs (Programmable Systems on Chip), computers, servers, tablets, cellular telephones, smart phones and computer units known to the person skilled in the art, or combinations of these. This computing unit may include a storage device, display device and/or a Human Interface Device (HID), may be or include a special purpose computing unit programmed to run the method of this disclosure.

A storage device includes, without limiting, RAM memory (cache memory, SRAM, DRAM, DDR), ROM memory (Flash, cache, HDD, SSD, EPROM, EEPROM, removable memory ROM (SD (miniSD, microSD, etc), MMC (MultiMedia Card), Compact Flash, SMC (Smart Media Card), SDC (Secure Digital Card), MS (Memory Stick), among others)), CD-ROM, Digital Versatile Disc (DVD) or other optical storage, magnetic cassettes, magnetic tapes, storage or any other means that can be used to store information and which can be accessed by a computer unit, among others known to those skilled in the art, and combinations of these. The storage device have memory registers, in which instructions, data structures and software modules stored.

A display includes, without limiting, monitors is anything capable of being connected to a computing unit and displaying its output. CRT monitor, flat panel display, Liquid Crystal D Liquid Crystal Display (LCD), active matrix LCD, passive matrix LCD, LED displays, display projectors, TV (4 KTV, HDTV, Plasma TV, Smart TV). OLED displays, AMOLED Displays, Quantum dot (QD) displays, segments displays, among other devices capable of showing data to a user, known to those skilled in the art, and combinations of these.

A HID includes, without limiting, keyboard, mouse, trackball, touchpad, pointing stick, joystick, touch screen, among other devices capable of allowing a user to input data into the computing unit of the tissue stimulating device, known to those skilled in the art, and combinations of these.

The decoupling circuit (23) makes it possible to electrically decouple the external power source (22) from the arrangement of electromagnetic transducers (1), said circuit may be constructed on optocouplers, relays, functional amplifiers, resistors, condensers, transformers, combination diodes of these and other electronic elements for electrically decoupling two electrical circuits or elements. The decoupling circuit also allows one to electrically isolate the tissue of interest from the external power source and guarantee fluctuations in the voltage which are dangerous for the tissue.

As used herein in the present disclosure, the switching circuit (40) may be selected from the group of multiplexers (digital multiplexer or analog multiplexers), demultiplexers (digital demultiplexer or analog demultiplexers), arrangement of transistors, circuits combining capacitors, diodes, resistors, operational amplificators, and combination of these providing commutation of data from a first electrical circuit to another electrical and the known to the person skilled in the art.

The switching circuit (40) allows switching between a number "n" of activation signal outputs (31-33) to a "k" number of activation signal outputs connected to each electromagnetic transducer of the arrangement of electromagnetic transducers (1), wherein "n" and "k" are natural numbers greater than zero. Optionally "n" is a value of between about 1 and about 1000, alternatively "n" is 1 and optionally 200, without being bounded to this values. Optionally "k" is a value of between about 1 and about 1000, alternatively "k" is 1 and optionally 200, without being bounded to this values.

It is possible for the device and the method of the present disclosure applying an electromagnetic field stimulus to a tissue according to an activation pattern for a determined period of time independently of the activation signal.

Also, in a particular example of the disclosure, the CPU (21a) generating an activation pattern to activate the electromagnetic transducers in the arrangement of electromagnetic transducers (1), the CPU (21a) then generating an activation signal which is received by electromagnetic transducers previously activated, thus the intensity and direction electromagnetic stimulation vector induced in the tissue vary according to the activation pattern in combination with the activation signal which vary the intensity.

The external power source (22) makes it possible to provide the electric power required for operation of the arrangement of electromagnetic transducers and may be a device capable of maintaining a voltage between two or more terminals such as a power source of alternating current, a power source of continuous current, batteries, photovoltaic power source, thermoelectric power source, among other devices capable of maintaining a voltage between two or more terminals known to the person skilled in the art, or combinations of these.

In turn, a volume (2) is understood as a body that occupies a three-dimensional space, the volume (2) may be a solid or may contain various spaces.

Activating an electromagnetic transducer or activating the arrangement of electromagnetic transducers (1) means providing electrical power to the electromagnetic transducers or to the arrangement of electromagnetic transducers (1).

An arrangement of electromagnetic transducers is a set of "n" electrical field transducers or magnetic field transducers, or a combination of these, with "n" being a natural number greater than or equal to 1.

Said electromagnetic transducers can be designated as electromagnetic transducers, which can be electrical field transducers or magnetic field transducers or can be configured by a combination of electrical field transducers and magnetic field transducers. Magnetic field transducers may also be designated as magnetic transducers and electric field transducers may also be designated as electrical transducers. In the case of the electrical field being the prevailing phenomenon, it is understood that said electromagnetic transducers are electrical field transducers, and in turn, when the prevailing phenomenon is the magnetic field, it is understood that the electromagnetic transducers are magnetic field transducers.

The electromagnetic transducers of the arrangement of electromagnetic transducers (1) have an active face in a geometric shape which is selected from, among others, the group of geometric figures such as squares, rectangles, circles, concentric rings, ovals and geometric figures known to a person skilled in the art, along with combinations of these.

The active face of a transducer is the surface of the transducer through which the intensity of the electrical field, the intensity of the magnetic field, or the intensity of the electromagnetic field produced by said transducer, has greater intensity.

Optionally, in the method disclosed, at step (a) in the arrangement of electromagnetic transducers (1), the electromagnetic transducers are selected from, a group consisting of engines, electrodes, photoelectric transducers, induction actuators, resistors, coils that generate magnetic fields for induction, antennas, parallel plates conductor materials, and combinations of these.

In reference to FIG. 1, for example, an arrangement of electromagnetic transducers (1) is disposed on the surface of a volume (2), which arrangement comprises from an electromagnetic transducer (1a) to an electromagnetic transducer (1e'), which, in the illustrated example, comprises pairs of transducers, a first pair of electromagnetic transducers comprised of a transducer (1a) and a transducer (1a'), a second pair of electromagnetic transducers, comprised by a transducer (1b) and a transducer (1b'), a third pair of electromagnetic transducers comprised of a transducer (1c) and a transducer (1c'), a fourth pair of electromagnetic transducers comprised of a transducer (1d) and a transducer (1d'), a fifth pair of electromagnetic transducers comprised of a transducer (1e) and a transducer (1e') Each pair of transducers face each other and are each oriented with their active face such that it targets the interior of the volume (2) containing a tissue (3) of interest. Optionally, the active faces of the transducers are directed toward the tissue (3).

This arrangement, along with the method of this disclosure, makes it possible to activate the electromagnetic transducers and to apply an electromagnetic field distributed in the interior of the volume (2) which contains the tissue (3), which makes it possible to stimulate the tissue (3) for extended periods of time or for short periods of time.

Optionally, after step (b), is a step of changing the activation pattern and returning to step (b), said change in the activation pattern can be executed by a user, can be programmed in a computing unit, or can be manually or automatically adjusted via the intensity feedback of the electromagnetic field, tissue (3) impedance in a computing unit. The variation of the pattern may suppress adverse effects to the tissue (3) or regulate the electromagnetic energy delivered by the electromagnetic transducers (1) or regulate the power of an external power source connected to the device for stimulating a tissue with electromagnetic fields.

Alternatively, in the method of the present disclosure, the change in the activation pattern may be sequential or random, changing on the basis of a measurement of the intensity of the electromagnetic field produced by the arrangement of electromagnetic transducers, of tissue impedance response feedback or a combination of these. For example, by using a Hall Effect sensor to measure the intensity of the electrical field, if a certain level of intensity of the magnetic field on the tissue (3) is exceeded, the time for application of the activation pattern is decreased in proportion to the increase of the intensity of the magnetic field on the tissue (3). Alternatively, in the method disclosed when changing in the activation pattern is executed on the basis of a measurement of tissue impedance response feedback, said change may be proportional to said measurement, for example, if the tissue impedance response is greater than a certain tissue impedance response level, the duty cycle of an activation signal of the activation pattern increases.

FIG. 2A, shows a system of Cartesian coordinates in three dimensions comprised of three planes orthogonally disposed to each other and intersected by the coordinated axes of the origin, designated "Ox", "Oy" and "Oz", in which system of Cartesian coordinates is represented an electromagnetic field vector that corresponds to a vector resulting from variation of the electrical field ($\vec{\varepsilon}$) and/or magnetic field ($\vec{B}$) with an angle α in relation to the plane created by axes "x" and "y".

In reference to FIG. 2A. FIG. 2B. FIG. 2C. FIG. 2D. FIG. 2E shows, in an example, a slice (3a) of a portion of tissue (3) in a plane formed by axes "x" and "y", an electromagnetic field vector with an angle α, said vector corresponding to that resulting from the variation of the electrical field ($\vec{\varepsilon}$) and/or magnetic field ($\vec{B}$) on the surface of the tissue (3) slice (3a); the magnitudes of the vector components in axes "x", "y" and "z" of the electromagnetic field representing the intensity of the electromagnetic field that results from the combination of electromagnetic transducers of the arrangement of active electromagnetic transducers (1) over a determined period of time. FIG. 2B, FIG. 2C. FIG. 2D, FIG. 2E are only examples and do not limit the electromagnetic field vector from being located in the origin of the plane formed by axes "x" and "y", said electromagnetic field vector, as well as the origin of the system of coordinates in three dimensions, can be at any point in space within the volume (2) containing the tissue (3).

In reference to FIG. 2B, angle α takes any value between 0 degrees and 360 degrees in relation to the plane formed by planes "x" and "y" with the method of this disclosure, by means of an activation pattern of the electromagnetic transducers of the arrangement of electromagnetic transducers (1).

In reference to FIG. 2C, angle α takes a value equal to 90 degrees in relation to the plane formed by planes "x" and "y" with the method of this disclosure, by means of an activation pattern of the electromagnetic transducers of the arrangement of electromagnetic transducers (1).

In an example, a pair of electrical field transducers from the arrangement of electromagnetic transducers (1) which comprises a first electrical field transducer (1e') on a plane parallel to the plane formed by the "x" and "y" axes has a determined distance on the positive "z" axis, a second electrical field transducer (1e) on a plane parallel to the plane formed by the "x" and "y" axes have a determined distance on the negative "z" axis, said pair of transducers may or may not be facing each other, and may or may not be aligned. For example, upon activating the first electrical field transducer (1e') and the second electrical field transducer (1e), supplying negative electrical potential to the first transducer in relation to the second transducer reinforces the electrical field vector component in the direction of the positive "z" axis (a equal to 90 degrees), if the polarities of said pair of electrical field transducers are inverted, the electrical field vector points in the direction of the negative "z" axis (a equal to 270 degrees).

In reference to FIG. 2D, angle α takes a value equal to 180 degrees in relation to the plane formed by planes "x" and "y" with the method of this disclosure, by means of an activation pattern of the electromagnetic transducers of the arrangement of electromagnetic transducers (1).

In reference to FIG. 2E, angle α takes a value equal to 360 degrees in relation to the plane formed by planes "x" and "y" with the method of this disclosure, by means of an activation pattern of the electromagnetic transducers of the arrangement of electromagnetic transducers (1).

In another example, a pair of electrical field transducers from the arrangement of electromagnetic transducers (1) which comprises a third electrical field transducer (1a') on a plane parallel to the plane formed by the "x" and "z" axes has a determined distance on the positive "x" axis, a fourth electrical field transducer (1a) on a plane parallel to the plane formed by the "x" and "z" axes have a determined distance on the negative "x" axis, said pair of transducers may or may not be facing each other, and may or may not be aligned. For example, upon activating the third electrical field transducer (1a') and the fourth electrical field transducer (1a), supplying negative electrical potential to the first transducer in relation to the second transducer reinforces the electrical field vector component in the direction of the positive "x" axis (a equal to 0 or 360 degrees), if the polarities of said pair of electrical field transducers are inverted, the electrical field vector points in the direction of the negative "x" axis (a equal to 180 degrees).

The electromagnetic field vector may be oriented in any direction in the space within the volume (2) containing the target tissue (3), and may also be positioned over any point within the volume (2).

In the figures from FIG. 3A to FIG. 5C, an example of the variation of the electrical field in the three-dimensional space upon applying an activation pattern is illustrated.

In the figures from FIG. 3A to FIG. 5C, the same disposition of the arrangement of electromagnetic transducers is illustrated as shown in FIG. 1, a system of Cartesian coordinates in three dimensions with three axes (x, y, z), a volume (2) centered on the origin of the system of Cartesian coordinates, an arrangement of electromagnetic transducers (1) comprising five pairs of transducers separated into three groups of transducers.

A first group of transducers: a first pair of electromagnetic transducers: transducer (1a) and a transducer (a') and a second pair of electromagnetic transducers: a transducer (1b) and a transducer (1b').

A second group of transducers formed by: a first pair of electromagnetic transducers: a transducer (1c) and a transducer (c') and a second pair of electromagnetic transducers: formed by a transducer (1d) and a transducer (1d').

A third group of transducers formed by: a pair of electromagnetic transducers: a transducer (1) and a transducer (1e').

The first group of transducers of the arrangement of electromagnetic transducers (1) is disposed radially on axis z at a distance Z1 from the origin, each pair of transducers in this group faces each other on its active face and is oriented such that their active faces point to the interior of the volume (2) which contains a target tissue (3), optionally the active faces of the transducers are in the direction of the tissue (3) and any plane parallel to the surface of the active faces of first pair of transducers is orthogonal to any plane parallel to the surface of the active faces of the second pair of transducers.

The second group of the arrangement (1) of the electromagnetic transducers is disposed radially around axis z at a distance Z2 from the origin, each pair of transducers of this group faces each other at their active faces, and is oriented such that its active faces point toward the interior of the volume (2) containing a target tissue (3), optionally, the active faces of the transducers are in the direction of the tissue (3) and any plane parallel to the surface of the active faces of the first pair of transducers is orthogonal to any plane parallel to the surface of the active faces of the second pair of transducers.

In the example shown in FIG. 3 to FIG. 5C Z1 is greater than Z2.

The third group of transducers of the arrangement of electromagnetic transducers (1) is disposed longitudinally on axis z at a positive distance Z3, the second transducer at a negative distance Z4, said pair of transducers in this group faces each other on its active face and is oriented such that their active faces point to the interior of the volume (2) which contains a target tissue (3), optionally the active faces of the transducers are in the direction of the tissue (3) and any plane parallel to the surface of the active faces of first pair of transducers is orthogonal to any plane parallel to the surface of the active faces of the second pair of transducers of the planes parallel to any of the other planes parallel to the active faces of the transducers of the arrangement of electromagnetic transducers (1).

In an example, a program from the computing unit that implements the method executes the three variation of the activation patterns of the electrical fields, in three different times: a first time t1, a second time t2 and a third time t3.

FIG. 3A shows, in t, the activation pattern activating transducer (1a) with negative polarity in relation to the polarity of transducer (1a'), said electrical field vector has components in two of the three dimensions in the positive direction of axis "x" and the negative direction of axis "y".

FIG. 3B is a top view of the activation pattern in t1.

FIG. 3C is a perpendicular front view of the plane formed by the "y" and "z" axes of the activation pattern in t1.

Figure 4A:
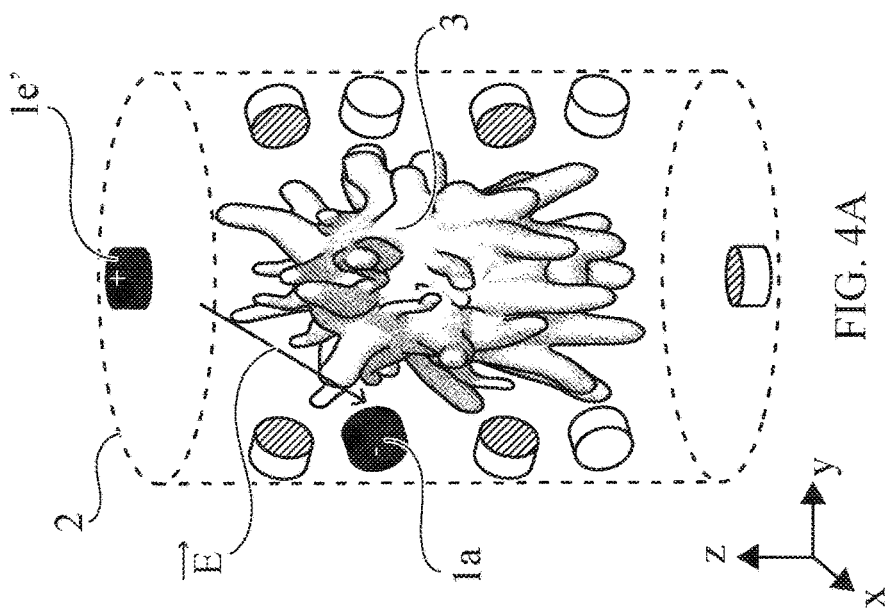
FIG. 4A shows a diagram of an arrangement of transducers in which the activation pattern of an initial time 2 activates a pair of electromagnetic transducers, in top view.

FIG. 4A shows, in t2, the activation pattern activating transducer (1a) with negative polarity in relation to the polarity of transducer (1e'), said electrical field vector has components in the three dimensions in the negative direction of axis "y" and the positive direction of axis "z".

Figure 4B:
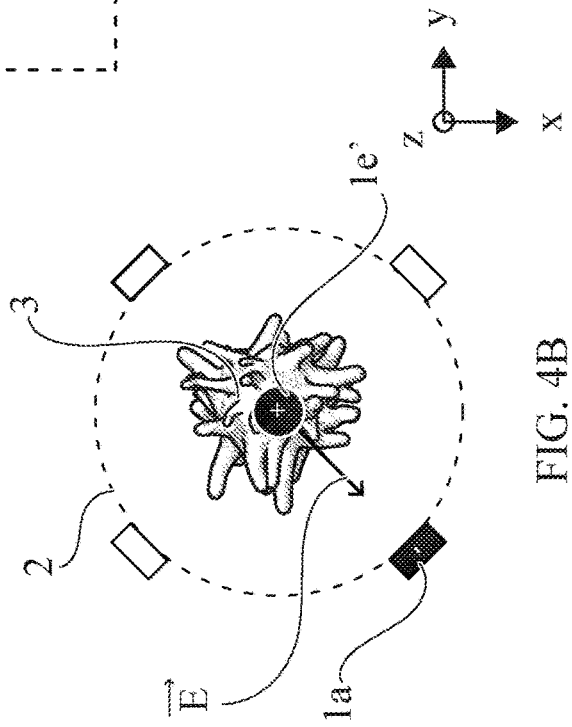
FIG. 4B shows a diagram of an arrangement of transducers in which the activation pattern of an initial time 2 activates a pair of electromagnetic transducers, in top view.

FIG. 4B is a top view of the activation pattern in t2.

Figure 4C:
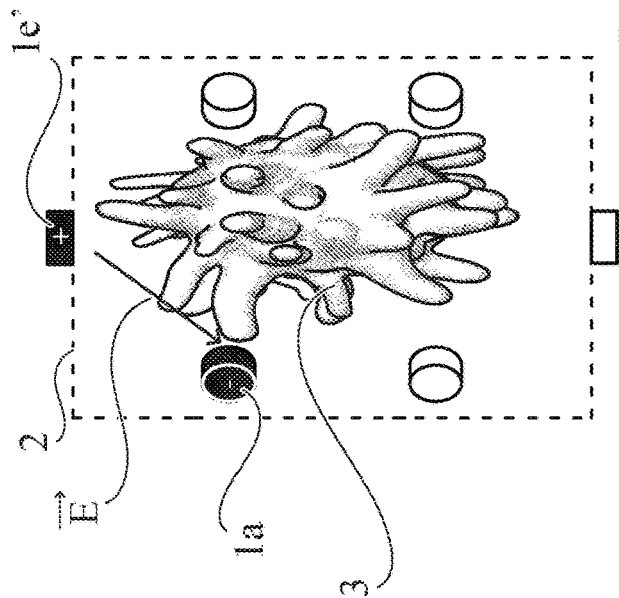
FIG. 4C shows a diagram of an arrangement of transducers in which the activation pattern of an initial time 2 activates a pair of electromagnetic transducers, in frontal view.

FIG. 4C is a perpendicular front view of the plane formed by the "y" and "z" axes of the activation pattern in t2.

FIG. 5A shows, in t3, the activation pattern activating transducer (1a) with negative polarity in relation to the polarity of transducer (1b), also activating transducer (1d) with positive polarity in relation to the polarity of transducer (1a) and equal polarity in relation to transducer (1b), said electrical field vector has components in the three dimensions in the negative direction of axis "y", negative direction of axis "y", and the positive direction of axis "z".

FIG. 5B is a top view of the activation pattern in t3.

FIG. 5C is a perpendicular front view of the plane formed by the "y" and "z" axes of the activation pattern in t3.

It is possible to apply a magnetic fields stimulation following the same diagram as the example described above and illustrated in the figures from FIG. 3A to FIG. 5C.

In an example of this disclosure, in step (a), the active face of each electromagnetic transducer of the arrangement of electromagnetic transducers (1) is in contact with the external surface of the tissue (3), such that it is necessary to provide less electrical potential to the electromagnetic transducers in order to stimulate the tissue (3), in comparison with another alternative in which the electromagnetic transducers are located a determined distance from the external surface of the tissue (3), whether or not, and in any case, the transducers are non-invasive of the tissue (3).

The external surface of the tissue (3) can be the skin of a subject, or organ reachable without surgically invasive implantation of the arrangement of electromagnetic transducers (1).

The intensity parameters and angle α of the electromagnetic field depend on the disposition and activation of the arrangement of electromagnetic transducers (I) encompassing the volume (2) containing a tissue (3).

In an example, at step (a), the active face of the electrical field transducers of the arrangement of electromagnetic transducers (1) is in contact with the external surface of the tissue (3), then the intensity of the electrical field generated by the electrical field transducers is between about 2 V/cm (volts per centimeter) and about 5 V/cm (volts per centimeter).

Alternatively, the intensity value of the electrical field for transducers having their active face in contact with the surface of the tissue may be selected among a range from about 2 V/cm to about 5 V/m, from about 2.1 V/cm to about 4.9 V/cm, from about 2.2 V/cm to about 4.8 V/cm from about 2.3 V/cm to about 4.7 V/cm, from about 2.4 V/cm to about 4.6 V/cm, from about 2.5 V/cm to about 4.5 V/cm, from about 2.6 V/cm to about 4.4 V/cm, from about 2.7 V/cm to about 4.3 V/cm, from about 2.8 V/cm to about 4.2 V/cm, from about 2.9 V/cm to about 4.1 V/cm, from about 3 V/cm to about 4 V/cm, from about 3.1 V/cm to about 3.9 V/cm from about 3.2 V/cm to about 3.8 V/cm, from about 3.3 V/cm to about 3.7 V/cm, from about 3.4 V/cm to about 3.6 V/cm, from about 2.2 V/cm to about 5 V/cm, from about 2.4 V/cm to about 5 V/cm, from about 2.6 V/cm to about 5 V/cm, from about 2.8 V/cm to about 5 V/cm, from about 3 V/cm to about 5 V/cm, from about 3.2 V/cm to about 5 V/cm, from about 3.4 V/cm to about 5 V/cm, from about 3.6 V/cm to about 5 V/cm, from about 3.8 V/cm to about 5 V/cm, from about 4 V/cm to about 5 V/cm, from about 4.2 V/cm to about 5 V/cm, from about 4.4 V/cm to about 5 V/cm, from about 4.6 V/cm to about 5 V/cm from about 4.8 V/cm to about 5 V/cm, from about 2 V/cm to about 4.8 V/cm, from about 2 V/cm to about 4.6 V/cm, from about 2 V/cm to about 4.4 V/cm, from about 2 V/cm to about 4.2 V/cm, from about 2 V/cm to about 4 V/cm, from about 2 V/cm to about 3.8 V/cm, from about 2 V/cm to about 3.6 V/cm, from about 2 V/cm to about 3.4 V/cm, from about 2 V/cm to about 3.2 V/cm, from about 2 V/cm to about 3 V/cm, from about 2 V/cm to about 2.8 V/cm, from about 2 V/cm to about 2.6 V/cm, from about 2 V/cm to about 2.4 V/cm, from about 2 V/cm to about 2.2 V/cm, from about 2.2 V/cm to about 2.4 V/cm, from about 2.4 V/cm to about 2.6 V/cm, from about 2.6 V/cm to about 2.8 V/cm, from about 2.8 V/cm to about 3 V/cm, from about 3 V/cm to about 3.2 V/cm, from about 3.2 V/cm to about 3.4 V/cm, from about 3.4 V/cm to about 3.6 V/cm, from about 3.6 V/cm to about 3.8 V/cm, from about 3.8 V/cm to about 4 V/cm, from about 4 V/cm to about 4.2 V/cm, from about 4.2 V/cm to about 4.4 V/cm, from about 4.4 V/cm to about 4.6 V/cm, from about 4.6 V/cm to about 4.8 V/cm, from about 4.8 V/cm to about 5 V/cm.

In Another example, in step (a), the active face of the magnetic field transducers that form the arrangement of electromagnetic transducers (1) is in contact with the external surface of the tissue (3), then the intensity of the magnetic field generated by the magnetic field transducers is between about 0.1 mT (mililteslas), equivalent to about 1 Gauss and about 200 mT (militeslas), equivalent to about 2000 Gauss.

Optionally, the intensity generated by the magnetic field transducers is selected among the range from about 1 mT to about 10 mT, from about 10 mT to about 20 mT, from about 20 mT to about 30 mT, from about 30 mT to about 40 mT, from about 40 mT to about 50 mT, from about 50 mT to about 60 mT, from about 60 mT to about 70 mT, from about 70 mT to about 80 mT, from about 80 mT to about 90 mT, from about 90 mT to about 100 mT, from about 100 mT to about 110 mT, from about 110 mT to about 120 mT, from about 120 mT to about 130 mT, from about 130 mT to about 140 mT, from about 140 mT to about 150 mT, from about 150 mT to about 160 mT, from about 160 mT to about 170 mT, from about 170 mT to about 180 mT, from about 180 mT to about 190 mT, from about 190 mT to about 200 mT, from about 1 mT to about 10 mT, from about 1 mT to about 20 mT, from about 1 mT to about 30 mT, from about 1 mT to about 40 mT, from about 1 mT to about 50 mT, from about 1 mT to about 60 mT, from about 1 mT to about 70 mT, from about 1 mT to about 80 mT, from about 1 mT to about 90 mT, from about 1 mT to about 100 mT, from about 1 mT to about 110 mT, from about 1 mT to about 120 mT, from about 1 mT to about 130 mT, from about 1 mT to about 140 mT, from about 1 mT to about 150 mT, from about 1 mT to about 160 mT, from about 1 mT to about 170 mT, from about 1 mT to about 180 mT, from about 1 mT to about 190 mT, from about 1 mT to about 200 mT, from about 1 mT to about 200 mT, from about 200 mT to about 190 mT, from about 190 mT to about 180 mT, from about 180 mT to about 170 mT, from about 170 mT to about 160 mT, from about 160 mT to about 150 mT, from about 150 mT to about 140 mT, from about 140 mT to about 130 mT, from about 130 mT to about 120 mT, from about 120 mT to about 110 mT, from about 110 mT to about 100 mT, from about 100 mT to about 90 mT, from about 90 mT to about 80 mT, from about 80 mT to about 70 mT, from about 70 mT to about 60 mT, from about 60 mT to about 50 mT, from about 50 mT to about 40 mT, from about 40 mT to about 30 mT, from about 30 mT to about 20 mT, from about 20 mT to about 10 mT.

In another example, in step (a), the active face of each transducer of the arrangement of electromagnetic transducers (1) is spaced apart from the external surface of the tissue (3), such that it is necessary to supply greater electrical potential in order to stimulate the tissue (3) in comparison with the alternative wherein the electromagnetic transducers are in contact with the external surface of the tissue (3), and is used even though it is not limited, for example, when it is not possible to make physical contact with the external surface of the tissue (3).

In an example, in step (a), the active face of the electrical field transducers of the arrangement of electromagnetic transducers (1) are spaced apart from the external surface of the tissue (3), the intensity of the electrical field generated by the electrical field transducers is between about 330 V/cm (volts per centimeter) and about 20000 V/cm (volts per centimeter) for fixed distances between the active face of the electrical field electromagnetic transducers and the surface of the tissue (3) between about 0.01 cm and about 50 cm and preferable between about 0.01 cm and about 4 cm.

Optionally, the intensity value of the electrical field for transducers located a fixed distance from the surface of the tissue may be selected among a range from about 0.33 kV/cm to about 20 kV/cm, from about 0.83 kV/cm to about 19.5 kV/cm, from about 1.33 kV/cm to about 19 kV/cm, from about 1.83 kV/cm to about 18.5 kV/cm, from about 2.33 kV/cm to about 18 kV/cm, from about 2.83 kV/cm to about 17.5 kV/cm, from about 3.33 kV/cm to about 17 kV/cm, from about 3.83 kV/cm to about 16.5 kV/cm, from about 4.33 kV/cm to about 16 kV/cm, from about 4.83 kV/cm to about 15.5 kV/cm, from about 5.33 kV/cm to about 15 kV/cm, from about 5.83 kV/cm to about 14.5 kV/cm, from about 6.33 kV/cm to about 14 kV/cm, from about 6.83 kV/cm to about 13.5 kV/cm, from about 7.33 kV/cm to about 13 kV/cm, from about 7.83 kV/cm to about 12.5 kV/cm, from about 8.33 kV/cm to about 12 kV/cm, from about 8.83 kV/cm to about 11.5 kV/cm, from about 9.33 kV/cm to about 1 kV/cm, from about 9.83 kV/cm to about 10.5 kV/cm, from about 1.33 kV/cm to about 20 kV/cm, from about 2.33 kV/cm to about 20 kV/cm, from about 3.33 kV/cm to about 20 kV/cm, from about 4.33 kV/cm to about 20 kV/cm, from about 5.33 kV/cm to about 20 kV/cm, from about 6.33 kV/cm to about 20 kV/cm, from about 7.33 kV/cm to about 20 kV/cm, from about 8.33 kV/cm to about 20 kV/cm, from about 9.33 kV/cm to about 20 kV/cm, from about 10.33 kV/cm to about 20 kV/cm, from about 11.33 kV/cm to about 20 kV/cm, from about 12.33 kV/cm to about 20 kV/cm, from about 13.33 kV/cm to about 20 kV/cm, from about 14.33 kV/cm to about 20 kV/cm, from about 15.33 kV/cm to about 20 kV/cm, from about 16.33 kV/cm to about 20 kV/cm, from about 17.33 kV/cm to about 20 kV/cm, from about 18.33 kV/cm to about 20 kV/cm, from about 19.33 kV/cm to about 20 kV/cm, from about 0.33 kV/cm to about 19 kV/cm, from about 0.33 kV/cm to about 18 kV/cm, from about 0.33 kV/cm to about 17 kV/cm, from about 0.33 kV/cm to about 16 kV/cm, from about 0.33 kV/cm to about 15 kV/cm, from about 0.33 kV/cm to about 14 kV/cm, from about 0.33 kV/cm to about 13 kV/cm, from about 0.33 kV/cm to about 12 kV/cm, from about 0.33 kV/cm to about 11 kV/cm, from about 0.33 kV/cm to about 10 kV/cm, from about 0.33 kV/cm to about 9 kV/cm, from about 0.33 kV/cm to about 8 kV/cm, from about 0.33 kV/cm to about 7 kV/cm, from about 0.33 kV/cm to about 6 kV/cm, from about 0.33 kV/cm to about 5 kV/cm, from about 0.33 kV/cm to about 4 kV/cm, from about 0.33 kV/cm to about 3 kV/cm, from about 0.33 kV/cm to about 2 kV/cm, from about 0.33 kV/cm to about 1 kV/cm, from about 1.33 kV/cm to about 2.33 kV/cm, from about 2.33 kV/cm to about 3.33 kV/cm, from about 3.33 kV/cm to about 4.33 kV/cm, from about 4.33 kV/cm to about 5.33 kV/cm, from about 5.33 kV/cm to about 6.33 kV/cm, from about 6.33 kV/cm to about 7.33 kV/cm, from about 7.33 kV/cm to about 8.33 kV/cm, from about 8.33 kV/cm to about 9.33 kV/cm, from about 9.33 kV/cm to about 10.33 kV/cm, from about 10.33 kV/cm to about 11.33 kV/cm, from about 11.33 kV/cm to about 12.33 kV/cm, from about 12.33 kV/cm to about 13.33 kV/cm, from about 13.33 kV/cm to about 14.33 kV/cm, from about 14.33 kV/cm to about 15.33 kV/cm, from about 15.33 kV/cm to about 16.33 kV/cm, from about 16.33 kV/cm to about 17.33 kV/cm, from about 17.33 kV/cm to about 18.33 kV/cm, from about 18.33 kV/cm to about 19.33 kV/cm, from about 19.33 kV/cm to about 20 kV/cm.

Alternatively, transducers may be located a distance from the surface of the tissue a distance selected among a range from about 0.01 cm to about 50 cm, from about 2 cm to about 48 cm, from about 4 cm to about 46 cm, from about 6 cm to about 44 cm, from about 8 cm to about 42 cm, from about 10 cm to about 40 cm, from about 12 cm to about 38 cm, from about 14 cm to about 36 cm, from about 16 cm to about 34 cm, from about 18 cm to about 32 cm, from about 20 cm to about 30 cm, from about 22 cm to about 28 cm, from about 24 cm to about 26 cm, from about 5 cm to about 50 cm, from about 10 cm to about 50 cm, from about 15 cm to about 50 cm, from about 20 cm to about 50 cm, from about 25 cm to about 50 cm, from about 30 cm to about 50 cm, from about 35 cm to about 50 cm, from about 40 cm to about 50 cm, from about 45 cm to about 50 cm, from about 0.01 cm to about 45 cm, from about 0.01 cm to about 40 cm, from about 0.01 cm to about 35 cm, from about 0.01 cm to about 30 cm, from about 0.01 cm to about 25 cm, from about 0.01 cm to about 20 cm, from about 0.01 cm to about 15 cm, from about 0.01 cm to about 10 cm, from about 0.01 cm to about 5 cm, from about 5 cm to about 10 cm, from about 10 cm to about 15 cm, from about 15 cm to about 20 cm, from about 20 cm to about 25 cm, from about 25 cm to about 30 cm, from about 30 cm to about 35 cm, from about 35 cm to about 40 cm, from about 40 cm to about 45 cm, from about 45 cm to about 50 cm.

In another example, in step (a), the active face of the transducers of the magnetic field of the arrangement of electromagnetic transducers (1) is spaced apart from the external surface of the tissue (3), the value of the intensity of the magnetic field on the tissue (3) generated by the magnetic field transducers is between about 0.1 mT (militeslas) equivalent to about 1 Gauss and about 200 mT (militeslas), equivalent to about 2000 Gauss, and optionally between about 40 mT (militeslas) equivalent to about 400 Gauss and about 200 mT (militeslas) equivalent to about 2000 Gauss.

In an example, in step (a), the active face of one of the electromagnetic transducers in the arrangement of electromagnetic transducers (1) is spaced apart from the external surface of the tissue (3).

In another example, in step (a), a portion of the area of the active face of the electromagnetic transducers of the arrangement of electromagnetic transducers (1) is in contact with the tissue (3) and the other portion of the area of the active face is spaced apart from the tissue (3), this configuration for the disposition of transducers makes it possible, for example, to stimulate a tissue (3) that is found in a volume (2) where the surface of said tissue (3) presents variations such that some portions tolerate physical contact with the active face of the transducer and other portions of the surface of the tissue (3) are difficult to access or not tolerated.

In an example, in step (a), a portion of the area of the active face of the electromagnetic transducers of the arrangement of electromagnetic transducers (1) is in contact with the tissue (3), in cases in which the surface area of the tissue (3) available for contact with the electromagnetic transducers is less than the area of the active face of the transducers, the tissue (3) can be stimulated with only a portion of the area of the active face of the electromagnetic transducers.

In an example of the method of the present disclosure, at step (a), the arrangement of electromagnetic transducers (1) is a unitary arrangement of magnetic field transducers, the magnetic field is generated via a single magnetic field electromagnetic transducer, or with various magnetic field electromagnetic transducers.

The activation signal received by the transducers of the arrangement of electromagnetic transducers (1), electrical field transducers, or magnetic field transducers may be a signal selected between a direct current or alternating current signal, a pulsed signal, a train of alternating or non-alternating impulsive signals, a square wave signal with variation of the duty cycle, triangular wave signal, sawtooth wave signal, modulated by amplitude (AM), modulated by frequency (FM), modulated by phase (PM), modulated by pulse positions (PPM), modulated by pulse width (PWM), and combinations of these. These signals are generated by a computing unit or by a signals generator or combinations of these, according to programs and feedback.

The programs cited by this disclosure correspond to information, coded or not, in a computing unit and which modify all of the parameters of the activation signal and the activation pattern activating the arrangement transducers (1). A unitary arrangement of transducers may be understood as an arrangement of electromagnetic transducers having one transducer.

In an example of the disclosure, at step (a), the arrangement of electromagnetic transducers (1) has two electrical field transducers which are activated simultaneously according to an activation pattern, for a determined period of time. These signals are generated by a computing unit or by a signals generator or combinations of these.

The signals generator can be selected from the group of professional wave generators, integrated circuits synthesizers DDS (Direct Digital Synthesizer)/DAC (Digital to Analog Conversion), NCO (Numerically Controlled Oscillator), arrays of operational amplifiers in wave generator configuration, bistable oscillator circuits and combinations of the above. The signal generator may also be named as wave generator.

In another example of the method of this disclosure, at step (a), the arrangement of electromagnetic transducers (1) is disposed over a frame (4) which encompasses the volume (2) and the purpose of which is to provide a support structure for the electromagnetic transducers that are disposed with their active face pointing toward the tissue (3) of interest.

In another example, the electromagnetic transducers of the arrangement of electromagnetic transducers (1) are disposed directly on the tissue (3) by means of a system of vacuum grippers activated manually, electronically, pneumatically, by an adhesive tape fastening system, or adhesives, velcro fastening systems or other fastening systems known to a person skilled in the art, or combinations of these.

Optionally, the system of vacuum grippers is on the active face of the electromagnetic gripper even though it is not limited to this position, the system of vacuum grippers makes it possible for the active face to be positioned over the surface of the target tissue (3) to be stimulated.

The frame (4) also can be used to change the shape of the surface of the volume (2) in order to obtain a plane surface that will make it possible to adjust the position of the electrical field transducers such that an optimal intensity of the electromagnetic field is obtained for stimulation of the tissue (3).

The frame (4) can be supported over the same tissue or be mechanically supported on a fixed or movable base. The type of frame (4) is chosen from the group comprised of shirts, vests, gloves, helmets, glasses, braces, stockings, boots, shoes, scarves, collars, and other structures that provide support to the transducers and combinations of them. In addition, the frame (4) can encompasses the volume (2) either totally or partially.

Optionally, the base on which the frame (4) is set can be movable in order to make it possible to move the arrangement (1) of transducers in relation to the surface of the volume (2) encompassing the tissue (3) and thus be able to reach different volumes encompassing different tissues and to vary the vector of the electromagnetic field.

Optionally, in step (a) of the method of this disclosure, the electromagnetic transducers of the arrangement of electromagnetic transducers (1) is spaced apart from the surface of the tissue (3) in the interior of the volume (2) encompassed by said arrangement.

In reference to FIG. 6A, a volume (2) containing a tissue (3), an arrangement of electromagnetic transducers (1) disposed such that it encompasses a volume (2), said arrangement of electromagnetic transducers (1) comprises a first electrical transducer (1a) with an active face (A) completely in contact with the external surface of the volume (2), facing a second electrical field transducer (1a') with an active face (1A') and in the direction of the tissue (3) in the interior of the volume (2), the active face (1A') of the second electrical field transducer (1a') is also completely in contact with the external surface of the volume (2).

In reference to FIG. 6B, a volume (2) containing a tissue (3), an arrangement of electromagnetic transducers (1) disposed such that it encompasses a volume (2), said arrangement of electromagnetic transducers (1) comprises a first electrical transducer (1a) with an active face (1A) partially in contact with the external surface of the volume (2), facing a second electrical field transducer (1a') with an active face (1A') and in the direction of the tissue (3) in the interior of the volume (2), the active face (1A') of the second electrical field transducer (a') is also partially in contact with the external surface of the volume (2).

Figure 7B:
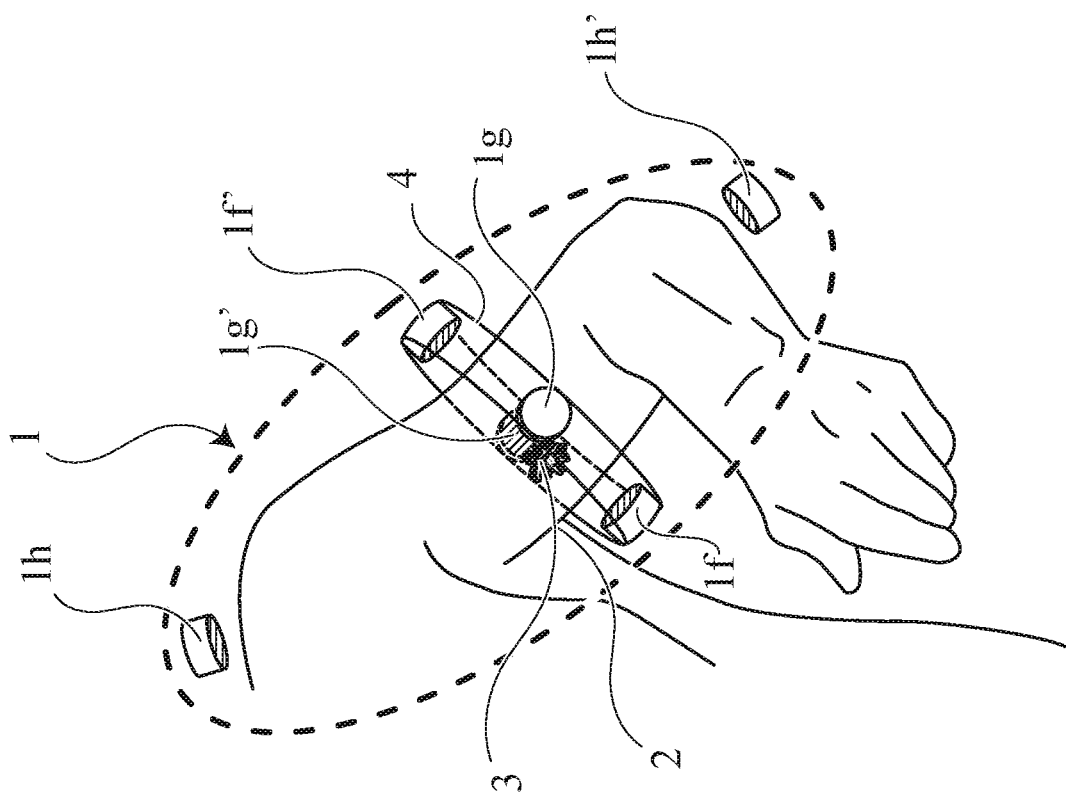
FIG. 7B shows an example of the placement of an arrangement of electromagnetic transducers without contact and targeting an arm tissue of an individual.
Figure 7A:
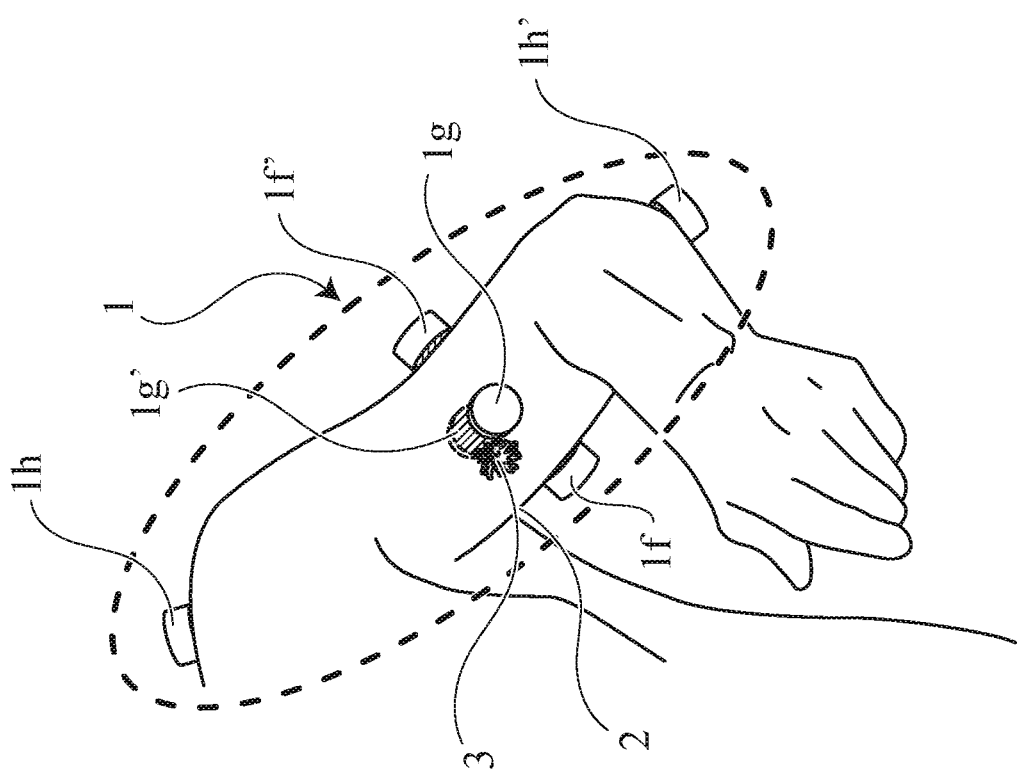
FIG. 7A shows an example of the placement of an arrangement of electromagnetic transducers in contact and targeting an arm tissue of an individual.

In addition, it is possible that the transducers that comprise each pair are not completely aligned nor parallel to each other, and it is also possible to stimulate the tissue (3) In reference to FIG. 7A illustrates the disposition of an arrangement of electromagnetic transducers (1) over a volume (2) which corresponds to the arm of an individual. In the interior of the arm is a tissue (3) which it is desired to stimulate electromagnetically.

Said arrangement of electromagnetic transducers (1) comprises two groups of transducers as detailed below:

A first group of transducers comprised by two pairs of electromagnetic transducers. A first pair of electromagnetic transducers: a transducer (1f) and a transducer (1f), a second pair of electromagnetic transducers: a transducer (1g) and a transducer (1g'), the first pair and the second pair of electromagnetic transducers are disposed radially around the humerus with their active faces in contact with the surface of the skin; a second group of transducers comprised by a pair of electromagnetic transducers: a transducer (1h) and a transducer (1h'), said pair of electromagnetic transducers is disposed over a plane normal to the axis of the humerus, the active face of the transducer (1h) over the shoulder and in contact with the skin, and the active face of the transducer (1h') over the elbow and in contact with the skin.

Each pair of transducers is disposed such that the active faces of the transducers that comprise said pair partially face each other, are aligned with their active faces in the direction of the position of the tissue (3) and with their active faces in contact with the skin.

It is also possible that the transducers that comprise each pair of transducers are not completely aligned or parallel to each other, or do not preserve the condition of orthogonality of the transducers described in the previous paragraph, may also succeed in stimulating the tissue (3).

There are various diagnostic tools for learning the location of the tissue (3), for example: magnetic resonance imaging, computerized tomography, PET (Positron Emission Tomography) scanning, x-rays. Doppler echography, electrocardiograms, diagnosis by palpation. Imaging-Guided Hookwire Localization, among others.

It is also possible to know the location of the tissue (3) using a measurement of tissue impedance response.

FIG. 7B illustrates a similar disposition of the transducers, but where the active faces of the transducers are separated a distance between about 0.01 cm and about 50 cm from the surface of the skin in the individual, supported on a frame (4), and optionally between about 0.01 cm and about 4 cm.

FIG. 8A illustrates the disposition of an arrangement of electromagnetic transducers (1) over a volume (2) which consists of the abdomen of an individual. In the interior of the abdomen is a tissue (3) which it is desired to stimulate electromagnetically. Said arrangement of electromagnetic transducers (1) comprising five groups of transducers as detailed below:

A first pair of transducers: a transducer (1i) and a transducer (i'), a second pair of transducers: a transducer (1j) and a transducer (1j'), a third pair of transducers: a transducer (1k) and a transducer (1k'), a fourth pair of transducers: a transducer (1l) and a transducer (1l').

Said pairs of transducers are disposed radially around an axis parallel to the spinal column, over the abdominal and dorsal area such that the active faces of the transducers face each other and in the direction of the position of the tissue (3) and with their active faces in contact with the skin.

Projections of the planes of the active faces of the transducers are arranged in the direction of the tissue and covering the maximum possible surface area of said tissue, with this configuration ensuring optimum stimulation of the tissue.

FIG. 8B illustrates a similar disposition of the transducers, but in which the active faces of the transducers are a distance of between 0.01 cm and 50 cm from the surface of the skin of the individual, supported on a frame (4), and optionally between 0.01 cm and 4 cm.

FIG. 9A illustrates the disposition of an arrangement of electromagnetic transducers (1) over a volume (2) which consists of the knee of an individual. In the interior of the knee is a tissue (3) which it is desired to stimulate electromagnetically. Said arrangement of electromagnetic transducers (1) comprising two pairs of transducers as detailed below:

A first pair of transducers: a transducer (1m) and a transducer (1m') and a second pair of transducers: a transducer (1n) and a transducer (1n').

Said pairs of transducers are disposed around the knee in the position of the tissue (3) at the height of the patella and such that the active faces of the transducers face each other in the direction of the position of the tissue (3).

FIG. 9B illustrates a similar disposition of the transducers, but in which the active faces of the transducers are separated a distance between about 0.01 cm and about 50 cm from the surface of the skin in the individual, supported on a frame (4), and optionally between about 0.01 cm and about 4 cm.

Optionally, in the arrangement of electromagnetic transducers (1), in an example of this disclosure, magnetic field electromagnetic transducers are positioned that do not require a transducer facing them to be operational, to make a magnetic field spatial scanning possible in accordance with the activation pattern for the electromagnetic transducers.

On the other hand, the arrangement of electromagnetic transducers (1) optionally meets a condition of orthogonality in that a plane parallel to any of the surfaces of the active faces of the each pair of transducers is orthogonal to a plane parallel to any of the surfaces of the active faces of the second, and third pair of transducers, and in addition, any plane parallel to the surfaces of the active faces of the other pairs of transducers inside the arrangement of electromagnetic transducers (1), and in addition, projections of the planes of the active faces pointed toward the tissue cover the maximum surface possible of said tissue (3), with this configuration ensuring optimum stimulation of the tissue (3).

It is also possible that the transducers of the arrangement of electromagnetic transducers (1) that comprise each pair are not completely aligned or parallel to each other, nor do they preserve the condition of orthogonality of the transducers described in the previous paragraph, may also succeed in stimulating the tissue (3).

Continuing to step (b) of the method of this disclosure, this is executed in a computing unit and the activation pattern follows the following steps:

step A) defining an electrical field transducers index with an initial value and a maximum number of pairs of electrical field transducers in the computing unit;

step B) selecting a pair of electrical field transducers from the arrangement of electromagnetic transducers (1) simultaneously in a position defined for the electrical field transducers index of step (A);

step C) activating the pair of electrical field transducers selected in step (B) with a determined polarity such that an electrical field transducer of said pair has positive electrical potential in relation to the other electric field transducer of said pair, during a determined period of time and going to step (D);

step E) deactivating the pair of electrical field transducers selected in step (B);

step F) increasing an electrical field transducers index and comparing the electrical field transducers index with the maximum number of pairs of pairs of electrical field transducers, if the electrical field transducers index is greater than the maximum number of pairs of electrical field transducers, making the electrical field transducers index equal to the value defined in step (A) and returning to step (B); if the electrical field transducers index is less than or equal to the maximum number of pairs of electrical field transducers, return to step (B);

wherein the electrical field transducers index is less than the maximum number of pairs of electrical field transducers, and the arrangement of electromagnetic transducers (1) has "n" pairs of electrical field transducers with "n" being a natural number greater than two.

Alternative, in step F) of step (b), the index value changes randomly and returns to step C).

Thus, the transducers can be activated randomly, and it is also possible to activate them in defined sequences, which will depend on the stimulation of the target tissue.

In addition, in step F) of step (b), the value of the index can change depending on tissue impedance response feedback and return to step C).

In an example of this disclosure, after step (C), there is a step (D) in which the polarity of the pair of electrical field transducers selected in step (B) is inverted in relation to the polarity of step (C), inverting the polarity to make abrupt changes in the electrical field vector possible.

Thus, the activation of the electrical field transducers can be achieved dynamically following tissue impedance response variations. For example, if the tissue has low impedance, stimulating for an extended time, increasing the duty cycle of the activation signal or increasing the amplitude of the activation signal.

In step (E), deactivating the pair of electrical field transducers corresponds to removing the electrical power supplied to the pair of electrical field transducers or providing the same electrical power to electrical field transducers.

Alternatively, in step (a), the arrangement of electromagnetic transducers (1) has at least two electrical field transducers and the disposition of said electrical field transducers is executed according to the following steps:

step a) positioning a first electrical field transducer (1a) in a first position such that the active face of the first electrical field transducer points in the direction of the tissue (3);

step b) positioning a second electrical field transducer (1a') in a second position such that its active face faces the active face of the first electrical field transducer (1a) positioned in step (a); and wherein the first electrical field transducer (1a) and the second electrical field transducer (1a') form a pair of joined activation transducers.

In step (b), the active face of the second transducer (1a') partially faces the active face of the first electrical field transducer (1a).

Optionally, after step (b), pairs of joined electrical field activation transducers are disposed subsequently from different positions following steps (a) and (b).

Alternatively, step (b) is executed in a computing unit and the activation pattern follows the following steps:

A) defining a magnetic transducers index and a maximum number of magnetic transducers;

B) selecting a magnetic field transducer from the arrangement of electromagnetic transducers simultaneously in a position defined for the magnetic field transducers index of step (A);

C) activating the magnetic transducer selected in step (B) for a determined period of time and going to step (D);

D) deactivating the magnetic transducer selected in step (B) and going to step (E);

E) increasing a magnetic transducers index and comparing the magnetic transducers index with the maximum number of magnetic transducers, if the magnetic transducers index is greater than the maximum number of magnetic transducers, make the magnetic transducers index equal to the value defined in step (A) and returning to step (B);

if the magnetic transducers index is less than or equal to the maximum number of magnetic transducers, return to step (B);

wherein the magnetic transducers index is less than the maximum number of magnetic transducers.

Alternatively, in step F) of step (b), the index value changes randomly and returns to step C).

In addition, it is possible that more than one magnetic field transducer is activated at the same time.

Said magnetic field transducers may or may not face each other with their active faces parallel over the surface of the tissue, in addition they may or may not be aligned with each other.

The magnetic field transducers can be activated randomly, and it is also possible to activate them in defined sequences, which will depend on the stimulation of the target tissue.

In addition, in another specific example, in step F) of step (b), the value of the index changes depending on tissue impedance response feedback and returns to step C).

Thus, the activation of the magnetic field transducers can be achieved dynamically following tissue impedance response variations. For example, if the tissue has low impedance, stimulating for an extended time, increasing the duty cycle of the activation signal or increasing the amplitude of the activation signal.

In step (D), deactivating the pair of magnetic field transducers corresponds to removing the electrical power supplied to the magnetic field transducer.

In addition to the above, tissue stimulation can also be applied by using frequency scanning, as described in the Colombian application NC2018/0001283 filed on 7 Feb. 2018.

In an example of a combination of the method of the present disclosure and the disclosure of the frequency scanning cited above, the tissue stimulation can be achieved using an activation pattern activating the transducers while simultaneously applying a specific activation signal through active transducers.

DEFINITIONS AND ACRONYMS

RAM Random Access Memory.
SRAM Static Random Access Memory.
DRAM Dynamic Random Access Memory.
DDR Memory Double Data Rate Memory.
ROM Read Only Memory.
HDD Hard Disk Drive.
SSD Solid State Drive.
EPROM Erasable Programmable Read-Only Memory.
EEPROM Electrically Erasable Programmable Read-Only Memory.
SMC Smart Media Card.
SDC Secure Digital Memory Card.
MS Memory Stick.
CD-ROM Compact Disc Read Only Memory.
DVD Digital Versatile Disc.
AM Amplitude Modulation.
EMG Electromyographs.
ECG Electrocardiographs.
SPMF Sequentially Programmed Magnetic Field.
AMOLED Active Matrix Organic Light Emitting Diode.
ASIC Application Specific Integrated Circuits.
CPLD Complex Programmable Logic Devices.
DSC Digital Signal Controllers.
EEG Electroencephalogram.
FM Frequency Modulation.
FPGA Field Programmable Gate Arrays.
HID Human Interface Device.
LCD Liquid Crystal Display.
LED Light Emitting Diode.
MFG Magnetic Field Generator.
OLED Organic Light Emitting Diode.

PM Phase Modulation.
PPM Pulse Position Modulation.
PSoC Programmable Systems on Chip.
PWM Pulse Width Modulation.
QD Quantum Display.
SoC Systems on Chip.

This disclosure is not limited to the described an illustrated examples, since, as will be obvious to the person skilled in the art, there are possible variations and modifications that do not depart from the spirit of the disclosure, which is only defined by the following claims.

The invention claimed is:

1. A method for electromagnetic stimulation of a tissue comprising the steps of:
   a) disposing an arrangement of electromagnetic transducers encompassing a volume containing a tissue; and
   b) applying an electromagnetic field stimulus to the tissue through the arrangement of electromagnetic transducers according to an activation pattern for a determined period of time;
   wherein step (b) is executed via a computing unit and the activation pattern follows the steps of:
   A) defining a magnetic field transducers index and a maximum number of magnetic field transducers;
   B) selecting a magnetic field transducer from the arrangement of electromagnetic transducers simultaneously in a position defined for the magnetic field transducers index of step (A);
   C) activating the magnetic field transducer selected in step (B) for a determined period of time and going to step (D);
   D) deactivating the magnetic field transducer selected in step (B) and going to step (E);
   E) increasing the magnetic field transducers index and comparing the magnetic field transducers index with the maximum number of magnetic field transducers,
      if the magnetic field transducers index is greater than the maximum number of magnetic field transducers, making the magnetic field transducers index equal to the value defined in step (A) and returning to step (B);
      if the magnetic field transducers index is less than or equal to the maximum number of magnetic field transducers, returning to step (B);
   wherein the electromagnetic transducers of the arrangement of electromagnetic transducers are arranged in at least two planes formed by an X axis and a Y axis, and said planes are distributed along a Z axis;
   wherein the activation pattern varies the intensity and direction of an electromagnetic field vector produced by the arrangement of electromagnetic transducers in a three-dimensional space.

2. The method of claim 1, wherein, after step (b), there is a step of changing the activation pattern and returning to step (b).

3. The method of claim 2, wherein changing the activation pattern is executed on the basis of a measurement of intensity of the electromagnetic field produced by the arrangement of electromagnetic transducers, on a tissue impedance response feedback or a combination of these.

4. The method of claim 1, wherein, at step (a), the arrangement of electromagnetic transducers is a unitary arrangement of magnetic field transducers.

5. The method of claim 1, wherein, at step (a), an active face of each electromagnetic transducer of the arrangement of electromagnetic transducers is spaced apart from an external surface of the tissue.

6. The method of claim 1, wherein, at step (a), an active face of one of the electromagnetic transducers in the arrangement of electromagnetic transducers is spaced apart from an external surface of the tissue.

7. A method for electromagnetic stimulation of a tissue comprising the steps of:
   a) disposing an arrangement of electromagnetic transducers encompassing a volume containing a tissue; and
   b) applying an electromagnetic field stimulus to the tissue through the arrangement of electromagnetic transducers according to an activation pattern for a determined period of time;
   wherein step (b) is executed via a computing unit and the activation pattern follows the steps of:
   A) defining a magnetic field transducers index and a maximum number of magnetic field transducers;
   B) selecting a magnetic field transducer from the arrangement of electromagnetic transducers simultaneously in a position defined for the magnetic field transducers index of step (A);
   C) activating the magnetic field transducer selected in step (B) for a determined period of time and going to step (D);
   D) deactivating the magnetic field transducer selected in step (B) and going to step (E);
   E) increasing the magnetic field transducers index and comparing the magnetic field transducers index with the maximum number of magnetic field transducers,
      if the magnetic field transducers index is greater than the maximum number of magnetic field transducers, making the magnetic field transducers index equal to the value defined in step (A) and returning to step (B);
      if the magnetic field transducers index is less than or equal to the maximum number of magnetic field transducers, returning to step (B);
   wherein the electromagnetic transducers of the arrangement of electromagnetic transducers are arranged in at least two planes formed by an X axis and a Y axis, and said planes are distributed along a Z axis;
   wherein the activation pattern varies the intensity and direction of an electromagnetic field vector produced by the arrangement of electromagnetic transducers in a three-dimensional space; and
   wherein the electromagnetic field stimulus provides an intensity of a magnetic field on the tissue, as follows: the magnetic field generated by the arrangement of electromagnetic transducers is between about 0.1 mT and 200 mT.

8. The method of claim 7, wherein, after step (b), there is a step of changing the activation pattern and returning to step (b).

9. The method of claim 7, wherein, changing the activation pattern is executed on the basis of a measurement of intensity of the electromagnetic field produced by the arrangement of electromagnetic transducers, on a tissue impedance response feedback or a combination of these.

10. The method of claim 7, wherein, at step (a), the arrangement of electromagnetic transducers is a unitary arrangement of magnetic field transducers.

11. The method of claim 7, wherein, at step (a), an active face of each electromagnetic transducer of the arrangement of electromagnetic transducers is spaced apart from an external surface of the tissue.

12. The method of claim 7, wherein, at step (a), an active face of one of the electromagnetic transducers in the arrangement of electromagnetic transducers is spaced apart from an external surface of the tissue.

13. A device for stimulating a tissue with electromagnetic fields comprising:
   a computing unit;
   an external power source connected to the computing unit;
   a decoupling circuit connected to the external power source and to the computing unit;
   a switching circuit connected to the external power source, to the decoupling circuit and to the computing unit; and
   an arrangement of electromagnetic transducers configured to encompass a volume containing the tissue, connected to the computing unit and to the switching circuit;
   wherein the computing unit implements a method for electromagnetic stimulation of the tissue, the method comprising the step of: applying an electromagnetic field stimulus to the tissue through the arrangement of electromagnetic transducers according to an activation pattern for a determined period of time;
   wherein the step of applying an electromagnetic field stimulus to the tissue through the arrangement of electromagnetic transducers is executed via the computing unit and the activation pattern follows the steps of:
      A) defining a magnetic field transducers index and a maximum number of magnetic field transducers;
      B) selecting a magnetic field transducer from the arrangement of electromagnetic transducers simultaneously in a position defined for the magnetic field transducers index of step (A);
      C) activating the magnetic field transducer selected in step (B) for a determined period of time and going to step (D);
      D) deactivating the magnetic field transducer selected in step (B) and going to step (E);
      E) increasing the magnetic field transducers index and comparing the magnetic field transducers index with the maximum number of magnetic field transducers,
         if the magnetic field transducers index is greater than the maximum number of magnetic field transducers, making the magnetic transducers index equal to the value defined in step (A) and returning to step (B);
         if the magnetic field transducers index is less than or equal to the maximum number of magnetic field transducers, returning to step (B);
   wherein the electromagnetic transducers of the arrangement of electromagnetic transducers are arranged in at least two planes formed by an X axis and a Y axis, and said planes are distributed along a Z axis; and
   wherein the activation pattern varies the intensity and direction of an electromagnetic field vector produced by the arrangement of electromagnetic transducers in a three-dimensional space.

14. The device of claim 13, wherein the computing unit is a special purpose computing unit comprising a central processor unit connected to at least one oscillator.

15. The device of claim 13, wherein a central processor unit comprised by the computing unit is also connected to a peripheral device selected from a memory unit, a database, a hard drive, a keyboard, a camera, a touchscreen display, a scanner, a display, and a printer.

16. A method for electromagnetic stimulation of a tissue comprising the steps of:
   a) disposing an arrangement of electromagnetic transducers encompassing a volume containing a tissue; and
   b) applying an electromagnetic field stimulus to the tissue through the arrangement of electromagnetic transducers according to an activation pattern for a determined period of time;
   wherein, step (b) is executed via a computing unit and the activation pattern follows the steps of:
      A) defining an electrical field transducers index with an initial value and a maximum number of pairs of electrical field transducers;
      B) selecting a pair of electrical field transducers from the arrangement of electromagnetic transducers simultaneously in a position defined for the electrical field transducers index of step (A);
      C) activating the pair of electrical field transducers selected in step (B) with a determined polarity such that an electrical field transducer of said pair has positive electrical potential in relation to the other electrical field transducer of said pair, during a determined period of time;
      D) deactivating the pair of electrical field transducers selected in step (B);
      E) increasing the electrical field transducers index and comparing the electrical field transducers index with the maximum number of pairs of electrical field transducers,
         if the electrical field transducers index is greater than the maximum number of pairs of electrical field transducers, making the electrical field transducers index equal to the value defined in step (A) and returning to step (B);
         if the electrical field transducers index is less than or equal to the maximum number of pairs of electrical field transducers, returning to step (B);
   wherein the arrangement of electromagnetic transducers has "n" pairs of electrical field transducers with "n" being a natural number greater than two.

17. A method for electromagnetic stimulation of a tissue comprising the steps of:
   a) disposing an arrangement of electromagnetic transducers encompassing a volume containing a tissue; and
   b) applying an electromagnetic field stimulus to the tissue through the arrangement of electromagnetic transducers according to an activation pattern for a determined period of time;
   wherein, step (b) is executed via a computing unit and the activation pattern follows the steps of:
      A) defining an electrical field transducers index with an initial value and a maximum number of pairs of electrical field transducers in the computing unit;
      B) selecting a pair of electrical field transducers from the arrangement of electromagnetic transducers simultaneously in a position defined for the electrical field transducers index of step (A);
      C) activating the pair of electrical field transducers selected in step (B) with a determined polarity such that an electrical field transducer of said pair has positive electrical potential in relation to the other electrical field transducer of said pair, during a determined period of time;
      D) deactivating the pair of electrical field transducers selected in step (B);
      E) increasing the electrical field transducers index and comparing the electrical field transducers index with the maximum number of pairs of electrical field transducers, if the electrical field transducers index is greater than the maximum number of pairs of electrical field transducers, making the electrical field transducers index equal to the value defined in step (A) and returning to step (B);

if the electrical field transducers index is less than or equal to the maximum number of pairs of electrical field transducers, returning to step (B);

wherein the arrangement of electromagnetic transducers has "n" pairs of electrical field transducers with "n" being a natural number greater than two;

wherein the electromagnetic transducers of the arrangement of electromagnetic transducers are arranged in at least two planes formed by an X axis and a Y axis, and said planes are distributed along a Z axis;

wherein the activation pattern varies the intensity and direction of an electromagnetic field vector produced by the arrangement of electromagnetic transducers in a three-dimensional space; and wherein the electromagnetic field stimulus provides an intensity of an electrical field on the tissue, as follows: the electrical field generated by the arrangement of electromagnetic transducers is between about 2 V/cm and about 5 V/cm.

18. A device for stimulating a tissue with electromagnetic fields comprising:

a computing unit;

an external power source connected to the computing unit;

a decoupling circuit connected to the external power source and to the computing unit;

a switching circuit connected to the external power source, to the decoupling circuit and to the computing unit; and an arrangement of electromagnetic transducers configured to encompass a volume containing the tissue, connected to the computing unit and to the switching circuit;

wherein the computing unit implements a method for electromagnetic stimulation of the tissue, the method comprising the step of applying an electromagnetic field stimulus to the tissue through the arrangement of electromagnetic transducers according to an activation pattern for a determined period of time;

wherein the step of applying an electromagnetic field stimulus to the tissue through the arrangement of electromagnetic transducers is executed via the computing unit and the activation pattern follows the steps of:

A) defining an electrical field transducers index with an initial value and a maximum number of pairs of electrical field transducers in the computing unit;

B) selecting a pair of electrical field transducers from the arrangement of electromagnetic transducers simultaneously in a position defined for the electrical field transducers index of step (A);

C) activating the pair of electrical field transducers selected in step (B) with a determined polarity such that an electrical field transducer of said pair has positive electrical potential in relation to the other electrical field transducer of said pair, during a determined period of time;

D) deactivating the pair of electrical field transducers selected in step (B);

E) increasing the electrical field transducers index and comparing the electrical field transducers index with the maximum number of pairs of electrical field transducers, if the electrical field transducers index is greater than the maximum number of pairs of electrical field transducers, making the electrical field transducers index equal to the value defined in step (A) and returning to step (B);

if the electrical field transducers index is less than or equal to the maximum number of pairs of electrical field transducers, returning to step (B);

wherein the arrangement of electromagnetic transducers has "n" pairs of electrical field transducers with "n" being a natural number greater than two.

* * * * *